(12) United States Patent
    Singh

(10) Patent No.: US 10,067,134 B2
(45) Date of Patent: *Sep. 4, 2018

(54) DIAGNOSIS OF BENIGN AND CANCEROUS GROWTHS BY MEASURING CIRCULATING TUMOR STEM CELLS AND SERUM ANNEXINA2

(71) Applicant: The Board of Regents of the University of Texas System, Austin, TX (US)

(72) Inventor: Pomila Singh, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 7 days.

This patent is subject to a terminal disclaimer.

(21) Appl. No.: 15/408,886

(22) Filed: Jan. 18, 2017

(65) Prior Publication Data

US 2017/0122952 A1    May 4, 2017

Related U.S. Application Data

(63) Continuation of application No. 13/135,141, filed on Jun. 27, 2011, now Pat. No. 9,581,599.

(60) Provisional application No. 61/398,642, filed on Jun. 28, 2010, provisional application No. 61/398,644, filed on Jun. 28, 2010.

(51) Int. Cl.
    *G01N 33/574*    (2006.01)

(52) U.S. Cl.
    CPC ............. *G01N 33/57492* (2013.01); *G01N 2333/4718* (2013.01)

(58) Field of Classification Search
    None
    See application file for complete search history.

(56) References Cited

U.S. PATENT DOCUMENTS

| | | |
|---|---|---|
| 5,786,213 A | 7/1998 | Singh et al. |
| 6,645,465 B2 | 11/2003 | Hanash et al. |
| 7,854,932 B2 | 12/2010 | Singh |
| 2010/0291193 A1 | 11/2010 | Singh et al. |
| 2011/0085986 A1 | 4/2011 | Singh |
| 2012/0034627 A1 | 2/2012 | Singh |

FOREIGN PATENT DOCUMENTS

| | | |
|---|---|---|
| WO | WO 2008/076454 A1 | 6/2008 |
| WO | WO 2011/093927 A1 | 8/2011 |

OTHER PUBLICATIONS

Gilbey et al (Journal of Clinical Pathology, 2004, vol. 57, pp. 903-911).*
Galanzha et al (Journal of Biophotonics, 2009, vol. 2, pp. 725-735).*
The abstract of Kanwar et al (Cancer Research, Apr. 15, 2010, vol. 70, No. 8, suppl. 1, Abstract No. 4254) (Year: 2010).*
Dittmar et al (Clinical and Experimental Metastasis, 2008, vol. 25, pp. 11-32) (Year: 2008).*
U.S. Appl. No. 61/398,642, filed Jun. 28, 2010, Singh.
U.S. Appl. No. 61/398,644, filed Jun. 28, 2010, Singh.
Allard et al., "Tumor Cells Circulate in the Peripheral Blood of All Major Carcinomas but not in Healthy Subjects or Patients with Nonmalignant Diseases," *Clinical Cancer Research*, 2004; 10:6897-6904.
Antolovic et al., "Heterogeneous detection of circulating tumor cells in patients with colorectal cancer by immunomagnetic enrichment using different EpCAM-specific antibodies," *BMC Biotechnology*, 2010; 10:35.
Bao et al., "Effects of Annexin II gene silencing by siRNA on proliferation and invasive potential of Jurkat lymphoma cells," *Zhonghua Xue Ye Xue Za Zhi*, May 2009; 30(5):303-306. Abstract only.
Barker et al., "Lgr$^{5+ve}$ Stem Cells Drive Self-Renewal in the Stomach and Build Long-Lived Gastric Units In Vitro," *Cell Stem Cell*, Jan. 2010; 6:25-36.
Barker et al., "Leucine-Rich Repeat-Containing G-Protein-Coupled Receptors as Markers of Adult Stem Cells," *Gastroenterology*, 2010; 138:1681-1696.
Cammareri et al., "Isolation and Culture of Colon Cancer Stem Cells," *Methods in Cell Biology*, 2008; 86:311-324.
Caplin et al., "Expression and processing of gastrin in pancreatic adenocarcinoma," *British Journal of Surgery*, 2000; 87(8):1035-1040.
Cobb et al., "Deletion of functional gastrin gene markedly increases colon carcinogenesis in response to azoxymethane in mice," *Gastroenterology*, 2002; 123(2):516-530.
Cobb et al., "Intestinal Expression of Mutant and Wild-Type Progastrin Significantly Increases Colon Carcinogenesis in Response to Azoxymethane in Transgenic Mice," *Cancer*, Mar. 2004; 100(6):1311-1323.
Cristofanilli et al., "Circulating Tumor Cells, Disease Progression, and Survival in Metastatic Breast Cancer," *N. Engl. J. Med.*, 2004; 351:781-791.
Dalerba et al., "Phenotypic characterization of human colorectal cancer stem cells," *PNAS*, Jun. 2007; 104(24):10158-63.

(Continued)

*Primary Examiner* — Karen A Canella
(74) *Attorney, Agent, or Firm* — Mueting, Raasch & Gebhardt, P.A.

(57) ABSTRACT

Provided herein is a method for diagnosing/prognosing a metastatic cancer in a subject by measuring and detecting one or more of CS-ANXA2, DCAMKL, Lgr5 or CS-ANAX2 and DCAMKL or CS-ANXA2 and Lgr5 positive circulating tumor stem cells in the subject's blood or plasma. Also provided is a method for distinguishing the presence of early stage primary cancer from advanced stage metastatic cancer in the subject by measuring and detecting AnnexinA2, CS-ANXA2 and DCAMKL-1 or Lgr5 in the blood or plasma. In addition, there is provided a method for distinguishing the presence of benign, pre-cancerous tumorous growths or cancerous tumors in the subject by measuring and detecting AnnexinA2 and circulating tumor stem cells positive for CS-ANXA2 and DCAMKL or CS-ANXA2 and Lgr5 in the blood or plasma.

9 Claims, 31 Drawing Sheets

(56) References Cited

OTHER PUBLICATIONS

Diaz et al., "Specific interaction of tissue-type plasminogen activator (t-PA) with annexin II on the membrane of pancreatic cancer cells activates plasminogen and promotes invasion in vitro," *Gut*, 2004; 53(7):993-1000.

Emoto et al., "Annexin II Overexpression Correlates with Stromal Tenascin-C Overexpression," *Cancer*, 2001; 92(6):1419-26.

Fan et al., "Expression of Lgr5 in human colorectal carcinogenesis and its potential correlation with β-catenin," *Int. J. Colorectal Dis.*, 2010; 25(5):583-590.

Flores et al., "Improving the yield of circulating tumour cells facilitates molecular characterisation and recognition of discordant HER2 amplification in breast cancer," *British Journal of Cancer*, 2010; 102:1495-1502.

Frohlich et al., "Enhanced expression of the protein kinase substrate p36 in human hepatocellular carcinoma," *Molecular and Cellular Biology*, 1990; 10(6):3216-3223.

Gerke et al., "Annexins: From Structure to Function," *Physiol. Rev.*, 2002; 82(2):331-71.

Hajjar et al., "An Endothelial Cell Receptor for Plasminogen/Tissue Plasminogen Activator," *The Journal of Biological Chemistry*, 1994; 269(33):21191-7.

Han et al., "Expression of Peripheral Blood CD44 in Patients with Colon Cancer," *Xiandai Zhongliu Yixue*, 2006; 14:967-969. Abstract only.

Horst et al., "The cancer stem cell marker CD133 has high prognostic impact but unknown functional relevance for the metastasis of human colon cancer," *The Journal of Pathology*, 2009; 219(4):427-434.

Huang et al., "Colon cancer stem cells: implication for prevention and therapy," *Trends in Molecular Medicine*, Nov. 2008; 14(11):503-509.

Inokuchi et al., "Annexin A2 positively contributes to the malignant phenotype and secretion of IL-6 in DU145 prostate cancer cells," *Int. J. Cancer*, 2009; 124:68-74.

Jacovina et al., "Homocysteine inhibits neoangiogenesis in mice through blockade of annexin A2-dependent fibrinolysis," *The Journal of Clinical Investigation*, 2009; 119(11):3384-94.

Ji et al., "Evaluation of annexin II as a potential serum marker for hepatocellular carcinoma using a developed sandwich ELISA method," *International Journal of Molecular Medicine*, 2009; 24:765-771.

Kalluri et al., "The basics of epithelial-mesenchymal transition," *The Journal of Clinical Investigation*, Jun. 2009; 119(6):1420-1428.

Kantara et al., "Inhibitory efficacy of curcumin ± stem cell specific RNAi on the growth of tumorospheres in vitro: Assay development and mechanisms of action," *AACR 102nd Annual Meeting* [online]. Abstract No. 4363. Apr. 2-6, 2011; Orange County Convention Center, Orlando, FL. [retrieved on Jan. 26, 2012]. Retrieved from the Internet:<URL:http://www.abstractsonline.com/Plan/AbstractPrintView.aspx?mID=2734&sKey=714e949>; 1 page.

Kantara et al., "Overexpression of Progastrin Imparts Tumorigenic/Metastatic Potential to Immortalized Embryonic Cells and Cancer Cells: Role of Stem/Progenitor Cell Markers and AnnexinA2," *Gastroenterology, AGA Abstracts*, Abstract No. 208, May 2011; 140(5), Suppl. 1: S-48.

Kim et al., "Enhanced expression of Annexin A4 in clear cell carcinoma of the ovary and its association with chemoresistance to carboplatin," *Int. J. Cancer*, 2009; 125:2316-2322.

Kim et al., "Immunosensors for detection of Annexin II and MUC5AC for early diagnosis of lung cancer," *Biosensors and Bioelectronics*, Oct. 2009; 25(2):456-462.

Ko et al., "High Percentage of False-Positive Results of Cytokeratin 19 RT-PCR in Blood: A Model for the Analysis of Illegitimate Gene Expression," *Oncology*, 2000; 59:81-88.

Koh et al., "Glycine-Extended Gastrin Promotes the Growth of Lung Cancer," *Cancer Res.*, 2004; 64:196-201.

Kokkinos et al., "Vimentin and Epithelial-Mesenchymal Transition in Human Breast Cancer—Observations in vitro and in vivo," *Cells Tissues Organs*, 2007; 185:191-203.

Lara et al., "Enrichment of Rare Cancer Cells Through Depletion of Normal Cells Using Density and Flow-Through, Immunomagnetic Cell Separation," *Experimental Hematology*, 2004; 32:891-904.

Li et al., "Identification of Pancreatic Cancer Stem Cells," *Cancer Research*, 2007; 67:1030-1037.

Lu et al., "Cloning and characterization of the annexin II receptor on human marrow stromal cells," *J. Biol. Chem.*, 2006; 281(41):30542-30550.

Lu et al., "Isolation of circulating epithelial and tumor progenitor cells with an invasive phenotype from breast cancer patients," *Int. J. Cancer*, Aug. 2009; 126(3):669-683.

Maheswaran et al., "Detection of Mutations in EGFR in Circulating Lung-Cancer Cells," *New Eng. J. Med.*, 2008; 359(4):366-377.

Maheswaran et al., "Circulating tumor cells: a window into cancer biology and metastasis," *Curr. Opin. Genet. Devel.*, Feb. 2010; 20(1):96-99.

May et al., "Identification of a Novel Putative Gastrointestinal Stem Cell and Adenoma Stem Cell Marker, Doublecortin and CaM Kinase-Like-1, Following Radiation Injury and in Adenomatous Polyposis Coli/Multiple Intestinal Neoplasia Mice," *Stem Cells*, 2008; 26(3):630-637.

May et al., "Doublecortin and CaM Kinase-like-1 and Leucine-Rich-Repeat-Containing G-Protein-Coupled Receptor Mark Quiescent and Cycling Intestinal Stem Cells, Respectively," *Stem Cells*, Aug. 2009; 27(1):2571-2579.

May et al., "Identification of a novel putative pancreatic stem/progenitor cell marker DCAMKL-1 in normal mouse pancreas," *Am. J. Physiol. Gastrointest. Liver Physiol.*, Jun. 2010; 299(2):G303-G310.

Mohammad et al., "Annexin A2 expression and phosphorylation are up-regulated in hepatocellular carcinoma," *Int. J. Oncol.*, 2008; 33:1157-1163.

Müller et al., "Insights into minimal residual disease in cancer patients: Implications for anti-cancer therapies," *Eur. J. Cancer*, May 2010; 46(7):1189-1197.

Myung et al., "Enhanced Tumor Cell Isolation by a Biomimetic Combination of E-selectin and Anti-EpCAM: Implications for the Effective Separation of Circulating Tumor Cells (CTCs)," *Langmuir*, 2010; 26(11):8589-8596.

Nagrath et al., "Isolation of rare circulating tumour cells in cancer patients by microchip technology," *Nature*, Dec. 2007; 450:1235-1239.

Navarro-Alvarez et al., "Isolation and Propagation of a Human CD133-Negative Colon Tumor Derived Cell Line With Tumorigenic and Angiogenic Properties," *Cell Transplantation*, 2010; 19(6):865-877.

Nedjadi et al., "S100A6 binds to annexin 2 in pancreatic cancer cells and promotes pancreatic cancer cell motility," *British Journal of Cancer*, 2009; 101:1145-1154.

Ohno et al., "Annexin II represents metastatic potential in clear-cell renal cell carcinoma," *British Journal of Cancer*, 2009; 101:287-294.

Ortiz-Zapater et al., "Tissue Plasminogen Activator Induces Pancreatic Cancer Cell Proliferation by a Non-Catalytic Mechanism That Requires Extracellular Signal-Regulated Kinase ½ Activation through Epidermal Growth Factor Receptor and Annexin A2," *Am. J. Pathol.*, May 2007; 170(5):1573-1584.

Papavasiliou et al., "Circulating tumor cells in patients undergoing surgery for hepatic metastases from colorectal cancer," *Proc (Bayl. Univ. Med. Cent.)*, Jan. 2010; 23(1):11-14.

Pituch-Noworolska et al., "Evaluation of Circulating Tumour Cells Expressing CD44 Variants in the Blood of Gastric Cancer Patients by Flow Cytometry," *Anticancer Research*, 1998; 18(5B):3747-3752.

Pituch-Noworolska et al., "Circulating Tumour Cells and Survival of Patients with Gastric Cancer," *Anticancer Research*, 2007; 27:635-640.

Rengifo-Cam et al., "Role of Progastrins and Gastrins and Their Receptors in GI and Pancreatic Cancers: Targets for Treatment," *Current Pharmaceutical Design*, Jul. 2004; 10(19):2345-2358.

(56) References Cited

OTHER PUBLICATIONS

Rengifo-Cam et al., "Antiapoptotic Effects of Progastrin on Pancreatic Cancer Cells Are Mediated by Sustained Activation of Nuclear Factor-κB," *Cancer Research*, 2007; 67:7266-7274.

Ricci-Vitiani et al., "Identification and expansion of human colon-cancer-initiating cells," *Nature*, Jan. 2007; 445:111-115.

Roitt, et al., "Immunology," Fifth Edition, 1998, Mosby International Ltd, London, UK; title page, copyright page, and p. 398.

Salnikov et al., "CD133 is indicative for a resistance phenotype but does not represent a prognostic marker for survival of non-small cell lung cancer patients," *Int. J. Cancer*, 2010; 126(4):950-958.

Sarkar et al., "Annexin A2 Mediates Up-regulation of NF-κK, β-catenin, and Stem Cell in Response to Progastrin in Mice and HEK-293 Cells," *Gastroenterology*, 2011; 140(2):583-595.

Scher et al., "Circulating tumour cells as prognostic markers in progressive, castration-resistant prostate cancer: a reanalysis of IMMC38 trial data," *The Lancet Oncology*, 2009; 10(3):233-239.

Serrano Fernández et al., "Clinical relevance associated to the analysis of circulating tumour cells in patients with solid tumours," *Clinical and Translational Oncology*, 2009; 11(10):659-668.

Sharma et al., "Angiogenesis-associated protein annexin II in breast cancer: Selective expression in invasive breast cancer and contribution to tumor invasion and progression," *Exp. Mol. Pathol.*, Oct. 2006; 81(2):146-156.

Sharma et al., "The role of annexin II in angiogenesis and tumor progression: a potential therapeutic target," *Curr. Pharm. Des.*, 2007; 13(35):3568-3575.

Sharma et al., "Breast cancer cell surface annexin II induces cell migration and neoangiogenesis via tPA dependent plasmin generation," *Experimental and Molecular Pathology*, 2010; 88(2):278-286.

Shiozawa et al., "Annexin II/Annexin II receptor axis regulates adhesion, migration, homing, and growth of prostate cancer," *J. Cell. Biochem.*, 2008; 105(2):370-380.

Shmelkov et al., "CD133 expression is not restricted to stem cells, and both $CD133^+$ and $CD133^-$ metastatic colon cancer cells initiate tumors," *J. Clin. Invest.*, 2008; 118(6):2111-2120.

Singh, P., "Role of Annexin-II in GI cancers: Interaction with gastrins/progastrins," *Cancer Letters*, 2007; 252(1):19-35.

Singh et al., "Role of Gastrin and Gastrin Receptors on the Growth of a Transplantable Mouse Colon Carcinoma (MC-26) in BALB/c Mice," *Cancer Research*, 1986; 46:1612-1616.

Singh et al., "Novel Gastrin Receptors Mediate Mitogenic Effects of Gastrin and Processing Intermediates of Gastrin on Swiss 3T3 Firbroblasts, Absence of Detectable Cholecystokinin (CCK)-A and CCK-B Receptors," *J. Biol. Chem.*, 1995; 270(15):8429-8438.

Singh et al., "Gastrin Gene Expression is Required for the Proliferation and Tumorigenicity of Human Colon Cancer Cells," *Cancer Research*, 1996; 56:4111-4115.

Singh et al., "Proliferation and differentiation of a human colon cancer cell line (CaCo2) is associated with significant changes in the expression and secretion of insulin-like growth factor (IGF) IGF-II and IGF binding protein-4: role of IGF-II," *Endocrinology*, 1996; 137(5):1764-1774.

Singh et al., "Mice overexpressing progastrin are predisposed for developing aberrant colonic crypt foci in response to AOM," *Am. J. Physiol. Gastrointest. Liver Physiol.*, 2000; 278:G390-G399.

Singh et al., "Progastrin expression predisposes mice to colon carcinomas and adenomas in response to a chemical carcinogen," *Gastroenterology*, 2000; 119(1):162-171.

Singh et al., "$Progastrin_{1-80}$ stimulates growth of intestinal epithelial cells in vitro via high-affinity binding sites," *Am. J. Physiol. Gastrointest. Liver Physiol.*, 2003; 284:G328-G339.

Singh et al., "Role of Gastrins in Colon Carcinogenesis," *Gastrin in the New Millenium*, 2004:319-327.

Singh et al., "Annexin II binds progastrin and gastrin-like peptides, and mediates growth factor effects of autocrine and exogenous gastrins on colon cancer and intestinal epithelial cells," *Oncogene*, 2007; 26:425-440.

Singh et al., "Targeting extra-cellular Annexin2 on epithelial cancer cells with labeled ligands for diagnosis/treatment of cancers," *AACR $101^{st}$ Annual Meeting 2010* [online]. Abstract No. 2585. Apr. 17-21, 2010; Walter E. Washington Convention Center, Washington, D.C. [retrieved on Jan. 27, 2012]. Retrieved from the Internet:<URL:http://www.abstractsonline.com/Plan/AbstractPrintView.aspx?mID=2521&sKey=0152bd2>; 1 page.

Singh et al., "T1152 Novel use of Progastrin Binding to Extracellular Annexin2 on Epithelial Cancer Cells for Diagnosis/Treatment of GI Cancers," *Gastroenterology*, May 2010; 138(5) Supp. 1:S-499.

Singh, Pomila "Annexina2/Progastrin and Stem Cells: Dietary Cancer Prevention," Grant Abstract, Grant No. 2R01CA097959-08 [online]. National Institutes of Health, project dates Dec. 1, 2002 to Aug. 31, 2016 [retrieved on Jan. 25, 2012]. Retrieved from the Internet:<URL:http://projectreporter.nih.gov/pr_Prj_info-desc dtls.dfm?aid=8107838&icde=11153375&p>; 2 pgs.

Soltanian et al., "Cancer stem cells and cancer therapy," *Tumor Biology*, 2011; 32(3):425-440.

Stott et al., "Isolation and Characterization of Circulating Tumor Cells from Patients with Localized and Metastatic Prostate Cancer," *Science Translational Medicine*, Mar. 2010; 2(25):25ra23.

Sureban et al., "Selective Blockade of DCAMKL-1 Results in Tumor Growth Arrest by a Let-7a MicroRNA-Dependent Mechanism," *Gastroenterology*, 2009; 137(2):649-659.e2.

Takano et al., "Annexin II Overexpression Predicts Rapid Recurrence after Surgery in Pancreatic Cancer Patients Undergoing Gemcitabine-Adjuvant Chemotherapy," *Ann. Surg. Oncol.*, 2008; 15(11):3157-3168.

Tanaka et al., "Circulating Tumor Cell as a Diagnostic Marker in Primary Lung Cancer," *Clinical Cancer Research*, 2009; 15(22):6980-6986.

Theodoropoulos et al., "Detection of Circulating Tumor Cells with Breast Cancer Stem Cell-Like Phenotype in Blood Samples of Patients with Breast Cancer," *Cancer Research*, 2008; 68; Abstract No. 2008.

Todaro et al., "Colon Cancer Stem Cells: Promise of Targeted Therapy," *Gastroenterology*, 2010; 138:2151-2162.

Umar et al., "Activation of NF-κb is required for mediating proliferative and antiapoptotic effects of progastrin on proximal colonic crypts of mice, in vivo," *Oncogene*, 2008; 27:5599-5611.

Umar et al., "Functional Cross-talk between β-Catenin and NFκB signaling Pathways in Colonic Crypts of Mice in Response to Progastrin," *J. Biol. Chem.*, 2009; 284(33):22274-22284.

Wu et al., "Precursor peptide $progastrin_{1-80}$ reduces apoptosis of intestinal epithelial cells and upregulates cytochrome c oxidase Vb levels and synthesis of ATP," *Am. J. Physiol. Gastrointest. Liver Physiol.*, 2003; 285:G1097-G1110.

Yan et al., "Increased Expression of Annexin A3 is a Mechanism of Platinum Resistance in Ovarian Cancer," *Cancer Res.*, 2010; 70(4):1616-1624.

Yang et al., "Optimization of an Enrichment Process for Circulating Tumor Cells from the Blood of Head and Neck Cancer Patients Through Depletion of Normal Cells," *Biotechnology and Bioengineering*, 2009; 102(2):521-534.

Yao et al., "Identification of metastasis associated proteins in human lung squamous carcinoma using two-dimensional difference gel electrophoresis and laser capture microdissection," *Lung Cancer*, 2009; 65(1):41-48.

Yasuda et al., "Elevated CD133, but not VEGF or EGFR, as a predictive marker of distant recurrence after preoperative chemoradiotherapy in rectal cancer," *Oncology Reports*, 2009; 22:709-717.

Yeung et al., "Cancer stem cells from colorectal cancer-derived cell lines," *Proc. Natl. Acad. Sci. USA*, 2010; 107(8):3722-3727.

Zeki et al., "Stem cells and their implications for colorectal cancer," *Nature Reviews Gastroenterology and Hepatology*, Feb. 2011, 8:90-100.

Zhang et al., "Anxa2 Plays a Critical Role in Enhanced Invasiveness of the Multidrug Resistant Human Breast Cancer Cells," *J. Proteome Res.*, 2009; 8(11):5041-5047.

(56) References Cited

OTHER PUBLICATIONS

Zhao et al., "Annexin II promotes invasion and migration of human hepatocellular carcinoma cells in vitro via its interaction with HAb18G/CD147," *Cancer Sci.*, Feb. 2010; 101(2):387-395.

Zhong et al., "Increased expression of Annexin A2 in oral squamous cell carcinoma," *Arch. Oral Biol.*, 2009; 54(1):17-25.

\* cited by examiner

Normal Colon   Adenoma   Adenocarcinoma

Normal   Hyperplastic   Adenoma   Adenocarcinoma

DCAMKL-1

CD44

LGR5

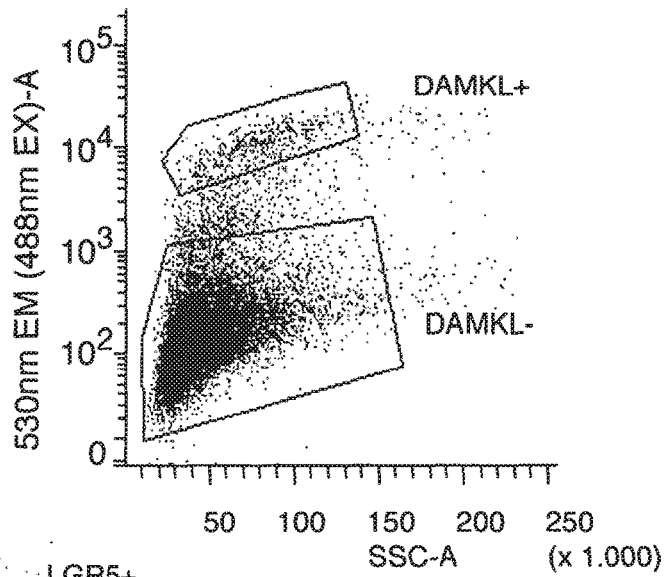
FIG. 7D
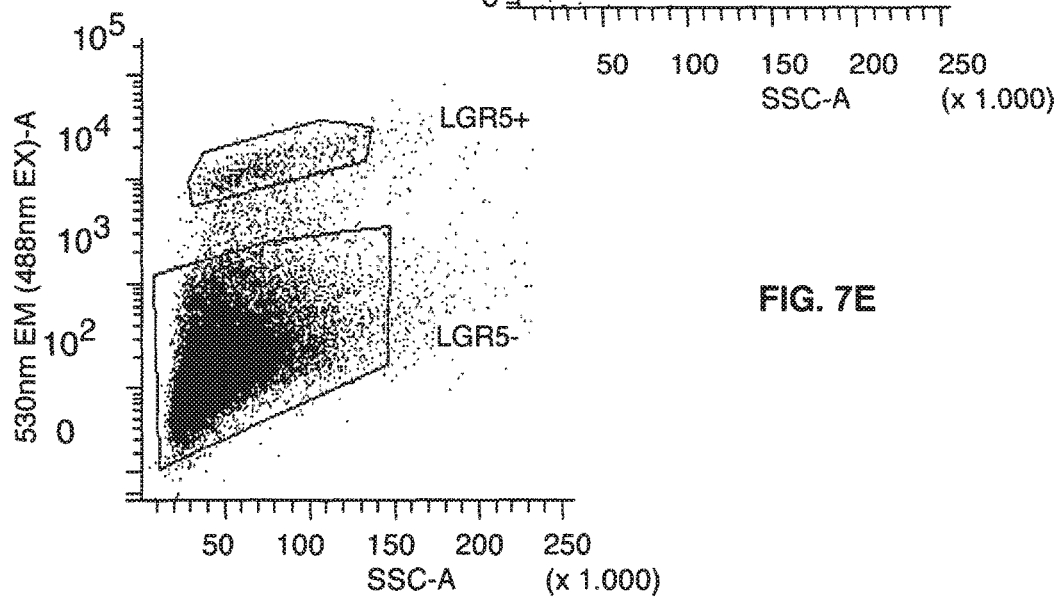
FIG. 7E
FIG. 7F
| Cell Lines | % Cells Positive for Indicated Markers | | |
|---|---|---|---|
| | ANXA2 | DCAM | LGR5 |
| HEK-C | 4 | 2.2 | 3.3 |
| HEK-mGAS | 10 | 5.7 | 4.3 |
| HCT-116 | 3.6 | 2.7 | 2.0 |
| KM12C | 3 | 3.5 | 2.8 |
| KM12L4 | 4.7 | 2.2 | 3.3 |

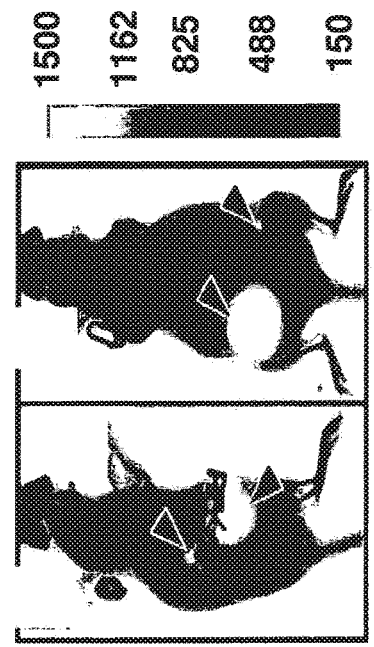
FIG. 8B
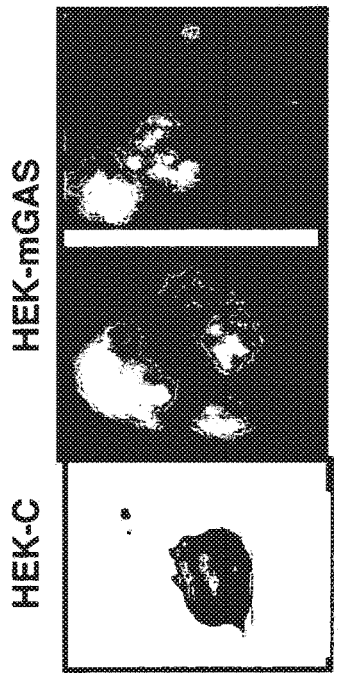
FIG. 8A
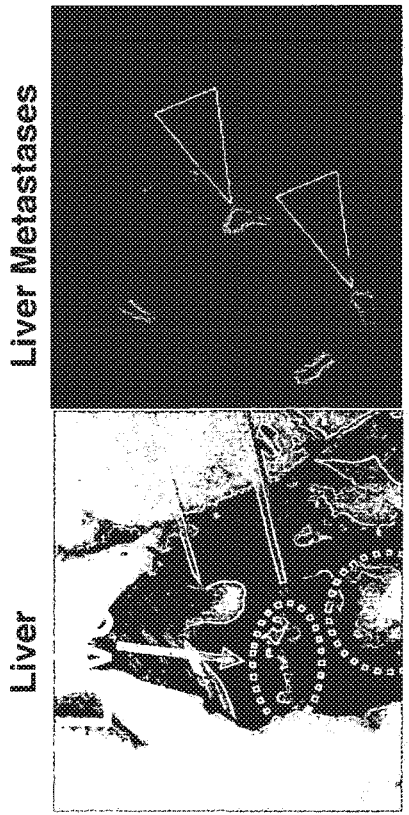
FIG. 8C
FIG. 8D

CD45 −

| IF Treatment | DCAMKL-1 (+) | | | CD44 (+) | | | LGR5 (+) | | | AnnexinA2 (+) | | |
|---|---|---|---|---|---|---|---|---|---|---|---|---|
| | N | PT | Met | N | PT | Met | N | PT | Met | N | PT | Met |
| Cells/mL of blood ~10^9 cells/mL | 0 cells | 40 cells | 60 cells | 60 cells | 200 cells | 220 cells | 20 cells | 100 cells | 160 cells | 40 cells | 120 cells | 200 cells |
| Total % cells/mL blood x10⁻⁶ | 0% | 0.4% | 0.6% | 0.6% | 2.0% | 2.2% | 0.2% | 1.0% | 1.6% | 0.4% | 1.2% | 2.0% |

Pellet CD45−

DCAMKL-1    ANNXA2    Merge

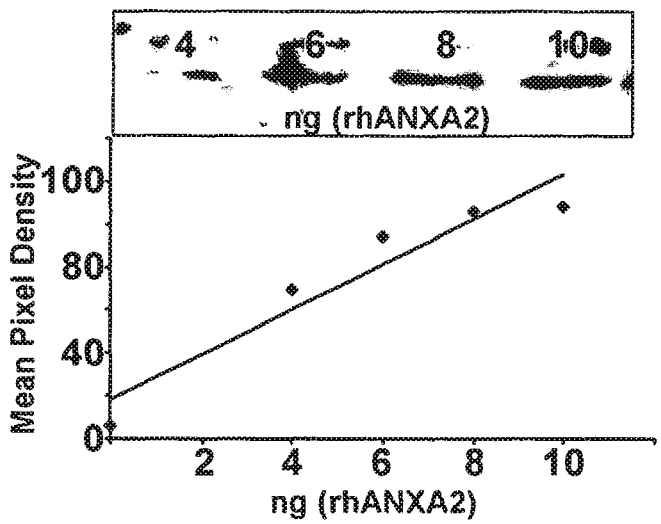
FIG. 22A
FIG. 22B
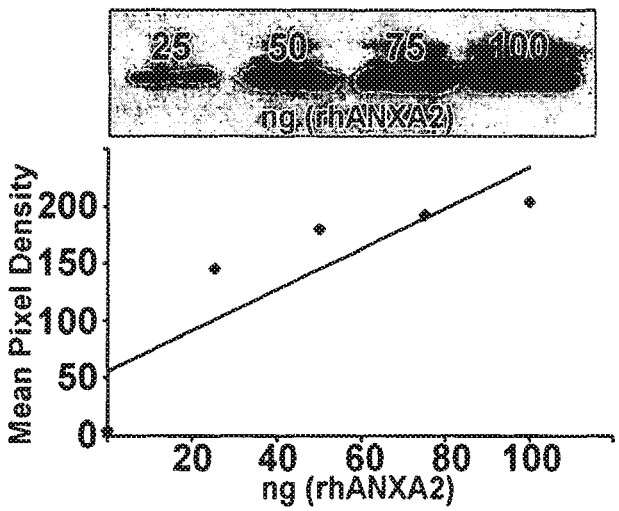
FIG. 22C
FIG. 22D
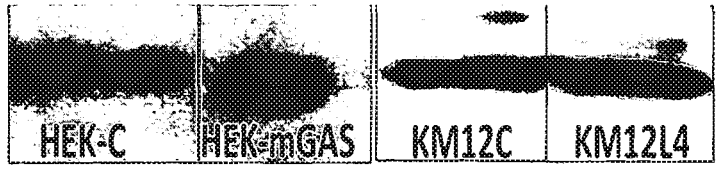
FIG. 22E

DIAGNOSIS OF BENIGN AND CANCEROUS GROWTHS BY MEASURING CIRCULATING TUMOR STEM CELLS AND SERUM ANNEXINA2

CROSS-REFERENCES TO RELATED APPLICATION

This nonprovisional application is a continuation of U.S. patent application Ser. No. 13/135,141, filed Jun. 27, 2011 which claims benefit of priority under 35 U.S.C. § 119(e) of provisional U.S. Ser. No. 61/398,642, filed Jun. 28, 2010, and U.S. Ser. No. 61/398,644, filed Jun. 28, 2010, the entireties of which are hereby incorporated by reference.

FEDERAL FUNDING

This invention was made with government support under Grant Number R01CA097959 awarded by the National Institutes of Health. The government has certain rights in the invention.

BACKGROUND OF THE INVENTION

Field of the Invention

The present invention relates generally to the fields of detection and diagnosis and, more specifically, to diagnosis of the presence of early stage (primary) or late stage (metastatic) cancerous tumors, using a combinatorial approach of measuring circulating tumor stem cells and serum AnnexinA2.

Description of the Related Art

Developing relatively simple, non-invasive methods for diagnosing the presence of either benign tumors, such as colonic hyperplasia, adenomatous polyps, or cancerous tumors, such as adenocarcinomas at different stages of the disease, has remained a challenge. Early stages of epithelial cancers are defined as cancerous tumors limited within the tissues of origin, e.g., primary tumors, while later stages of cancer represent metastatic growths either within the lymph nodes or at distant sites away from the primary cancerous growth, such as metastatic growths in the lung/liver of colorectal carcinomas. With the advent of sophisticated proteomics in the past 7 years, investigators discovered that AnnexinA2 (ANXA2) is increasingly expressed by epithelial tumors in relation to stage of the disease (1-16). AnnexinA2 is normally present intracellularly and performs important functions of cellular trafficking (17). However, rapidly proliferating tumor cells (especially at leading edges of tumors) express membrane-associated extracellular, cell-surface associated AnnexinA2 (CS-ANXA2) (1-3,8,10-16, 18). Other members of Annexin family (Annexin A4, Annexin A3) are reportedly over-expressed in ovarian cancers, and increase chemo resistance (19,20). Both tetrameric and monomeric forms of AnnexinA2 have been described on cell surface of endothelial and tumor cells (12,21).

As described above, surface-associated ANXA2 (CS-ANXA2) is increasingly expressed by many solid tumors, including colorectal (CRCs) and pancreatic cancers. ANXA2 lacks transmembrane domains and is tethered to the cell surface by binding to a 26Kda transmembrane protein (11,31). Surface-associated ANXA2 was significantly increased in colorectal adenomas and adenocarcinomas vs corresponding normal colonic mucosa (18).

Measuring circulating tumor cells in the blood of patients is a relatively new concept for diagnosing cancer, and is as yet in its infancy (52-55). Presence of circulating tumor cells likely predicts metastasis, and can be useful for monitoring recurrence (relapse) of the disease, post-treatment (56-60). Circulating tumor cells are detected by using many different methods, including immunocytochemistry (IHC) for epithelial markers such as cytokeratine-19 (CK19), and RT-PCR analysis for cancer-cell specific transcripts (61,62). Efficiency of such tests are poor, because of the rare presence of cancer cells within a very large number of blood cells (1-1000 CTCs in $10^9$ blood cells/ml blood). Negative selection by excluding blood cells has been used to enumerate circulating tumor cells (63). Positive selection of circulating tumor cells using antibodies (Abs) against epithelial cell surface proteins such as cell adhesion protein EpCAM is currently being used (64). Circulating tumor cells, positive for EpCAM, are captured using microfluoridic CTC-Chip devices (64) and immunomagnetic bead-based methods (18, 57). Isolated circulating tumor cells are confirmed by CK19 staining or Her2 amplification (53,65). Negative staining for CD45 (a Leukocyte marker) is also used (52). It is postulated that invasive cancer cells, going through epithelial mesenchymal transition (EMT), lose expression of cell surface EpCAM (66). Thus invasive circulating tumor cells, with the highest metastatic potential, may be under-evaluated using anti-EpCAM Abs (52,66,67). Besides, efficacy of different EpCAM-Abs for capturing circulating tumor cells differs significantly (68). Thus, there is a recognized need in the art for efficient and effective methods of measuring circulating tumor cells.

The presence of CTCs in the blood will not detect the presence of benign tumors at a pre-cancerous stage, such as adenomatous polyps growing in the colon of the patients. The escape of cancer cells from a pre-cancerous growth, such as adenomas, is much less likely since the basement membrane for such tumors is still intact. However, the pre-cancerous benign tumorous growths are well vascularized with blood vessels, and tumor-specific antigens can be secreted into the blood supply. Significant levels of AnnexinA2 are present in the serum of patients with breast (2,3), hepatocellular (17), and lung (79) cancers. So while one can potentially diagnose and predict the presence of cancerous tumors using the newly described assays for either circulating tumor cells or cancer specific antigens, such as Her/neu, PSA or AnnexinA2, no diagnostic tests have been described to predict the presence of pre-cancerous, benign tumors (such as colon polyps) in the patients.

There is thus a recognized need in the art for effective methods of detecting the presence of benign pre-cancerous tumors, before they convert into cancerous growths, as a preventative measure. The present invention fulfills this long-standing need and desire in the art.

SUMMARY OF THE INVENTION

The present invention is directed to a method of distinguishing the presence of benign, pre-cancerous tumorous growths in an individual from a subject who lacks the presence of either benign or cancerous growths by measuring the amount of AnnexinA2 in the blood or serum of the individual, in combination with measuring the presence of circulating tumor stem cells, positive for CS-ANXA2 and stem cell markers DCAMKL and Lgr5 in the blood or plasma of the individual. Presence of significant levels of AnnexinA2 in the blood or serum of the subject in the absence of any detectable circulating tumor stem cells positive for CS-ANXA2 or DCAMKL or Lgr5 is diagnostic/ prognostic for the presence of benign, pre-cancerous tumorous growths in the individual, in the absence of cancerous tumors.

The present invention is also directed to a method of distinguishing the presence of early stage cancers (primary cancer) from late stage cancers (metastatic cancers) in a subject in need of such treatment, comprising the step of measuring the amount of AnnexinA2 in the blood or serum of said subject.

The present invention is further directed to a method of identifying whether a subject has or will have a metastatic cancer, comprising the step of measuring circulating tumor stem cells positive for CS-ANXA2 and stem cell markers DCAMKL-1 or Lgr5 in blood or plasma of said individual, wherein the presence of CS-ANXA2+DCAMKL-1 or Lgr5 positive circulating tumor stem cells is diagnostic/prognostic for metastatic cancer or relapse of the cancer disease.

Other and further objects, features, and advantages will be apparent from the following description of the presently preferred embodiments of the invention, which are given for the purpose of disclosure.

BRIEF DESCRIPTIONS OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A-1B depict the role of ANXA2 in endocytosis of PG. FIG. 1A: The presence of cell-surface associated AnnexinA2 (CS-ANXA2) on IEC18 cells was confirmed by FACScan. The fluorescence intensity of cells labeled with anti-ANXA2-Abs was increased >10 fold compared to cells labeled with control IgG. FIG. 1B: IEC18 cells, cultured on glass coverslips, were stimulated with PG for 0-30 min and labeled with fluorescent Abs against ANXA2 (green) and PG (red) and imaged at 60× by confocal microscopy. Representative images at 0, 10 and 30 min are presented in FIG. 1B.

FIGS. 2A-2B are specimens processed for IF staining with anti-ANXA2-IgG and DAPI and co-localization PG/ANXA2 in human colon. FIG. 2A: Paraffin-embedded sections from representative normal colon, Ad and AdCA specimens from patients, processed for IF staining with anti-ANXA2-IgG and DAPI (for nuclear staining) is shown. FIG. 2B: Co-localization PG/ANXA2 in human colon. Paraffin embedded sections of normal human colon and colon tumors were stained for ANXA2 and Progastrin using specific Abs and detected by secondary Abs coupled to either Alexa 488 (Anti-mouse) or 594 (Anti-rabbit). Bottom panels show magnified view of the marked insets FIGS. 3A-3D show that PG up-regulates DCAMKL-1 and CD44 expression in colonic crypts of C57Bl/J6 mice. FIG. 3A: C57Bl/J6 Mice were injected with 0 nM, 1 nM and 10 nM recombinant human progastrin (rhPG) twice a day for 10 days. Colonic crypts were then isolated from the mice and measured for their lengths. FIG. 3B: Representative tissue sections from mid-colons of mice, treated with either saline (OnM) or 10 nM-rhPG. Dashed lines represent average length of colonic crypts in the indicated mice. FIG. 3C: Immunoblots of saline (0 nM) versus 10 nM-rhPG treated mice are shown. The expression of DCAMKL-1 and CD44 was analyzed. FIG. 3D: Mouse colon sections from the saline (OnM) and 10 nM-rhPG treated mice were processed for immunofluorescence (IF) staining with either anti-DCAMKL+1-IgG (green) or anti-CD44-IgG (red). Relative staining/cell for both DCAMKL+1/CD44 is increased in 10 nM PG colonic crypts.

FIGS. 4A-4E show that ANXA2 expression is required for the growth/signaling effects of progastrin in vivo. FIG. 4A: Representative immunoblot data demonstrating absence of AnxA2 expression in colonic crypts of ANXA2−/− mice. FIG. 4B: Representative tissue sections from mid-colons of ANXA2+/+/ANXA2−/− mice, treated with either saline (OnM) or 10 nM-rhPG. Dashed lines represent average length of colonic crypts in the indicated mice. FIG. 4C: To obtain accurate measurements of colonic-crypt lengths, colons were processed for preparation of isolated colonic-crypts, and lengths measured. Each bargraph=mean±SEM of 30-50 isolated-crypt lengths from 3-5 mice. *=p<0.05 versus control (saline-treated) mice;†=p<0.05 versus respective ANXA2+/+ levels. FIG. 4D: Isolated colonic crypts from mid-colons of the indicated genotypes were processed for immunoblot analysis. Representative blots of 6-8 blots from 3-4 mice are shown in FIG. 4D. Percent change in the ratio of p65Ser276:total p65 and β-catenin:β-actin, is shown in FIG. 4E; each group represents mean±SEM of data from 3-5 separate mice. *=p<0.05 versus corresponding-control (OnM PG) group.

FIGS. 5A-5D show that AnxA2 expression is required for stimulatory effect of progastrin on CD44/DCAMKL+1 expression in colonic crypts. Colonic crypts were isolated from the mice and processed for immunoblot analysis. Immunoblots from a representative mouse, of a total of 3-5 mouse blots, are shown in FIG. 5A. Immunoblot data from all the mice are presented in FIG. 5B, as percent change in the ratio of indicated proteins:β-actin. *=p<0.05 versus corresponding control (OnM PG) values. FIG. 5C: Mouse colon sections from the indicated 4 groups of mice were processed for immunofluorescence staining with either anti-DCAMKL+1-IgG (green) or anti-CD44-IgG (red). Representative enlarged images from stained colonic crypts of indicated mice are presented in FIG. 5C. Relative staining/cell for both DCAMKL+1/CD44 is increased in PG-treated ANXA2+/+ colonic crypts, but no significant differences were observed in PG-treated ANXA2−/− mice compared to corresponding controls. The percent cells (within a viewing field at 20× magnification) positive for either DCAMKL+1 or CD44 were counted in ten sections from 3-5 mice. Data are presented as mean±SEM in FIG. 5D. *=p<0.05 versus corresponding control mouse sections; †=p<0.05 versus corresponding ANXA2+/+ levels.

FIGS. 6A-6K shows that over-expression of PG in HEK-293 cells induced activation of NFκB and β-catenin pathways resulting in an increase in stem cells populations. FIG. 6A: Representative immunoblot data demonstrating full length PG expression in HEK-mGAS cells vs HEK—C cells. FIG. 6B: Representative immunoblot data demonstrating the relative expression of NFκB and its downstream target cox-2 in HEK-mGAS cells vs HEK—C cells. FIG. 6C: Representative immunoblot data demonstrating the relative expression of β-catenin, c-myc and cyclin-D1 in HEK-mGAS cells vs HEK—C cells. FIG. 6D: β-catenin promoter activity assay-HEK—C/HEK-mGAS cells, were transfected with either FOPFlash or TOPFlash plasmids and 24 h after transfection, promoter-activity was measured in terms of luciferase-units. FIG. 6E: P65 DNA binding assay-HEK—C/HEK-mGAS nuclear cell extracts were prepared and processed for measuring binding of activated-NF-κB in a DNA-binding-assay. FIG. 6F: HEK—C/HEK-mGAS cells growing on cover-slips were stained for the indicated stem cell marker DCAMKL-1 (FIG. 6F), CD44 (FIG. 6G) and LGR5 (FIG. 6H). Representative immunoblot demonstrating expression levels of DCAMKL-1 and CD44 in HEK—C/HEK-mGAS cells are shown in FIGS. 6I-6K.

FIGS. 7A-7F show measurements of ANXA2 in various cells. FIG. 7A: Western blot (WB) of ANXA2 in cellular lysates of HEK—C and HEK-mGAS cells. β-actin was run as controls. FIGS. 7B-7F are FACS data with antibodies against indicated proteins from HEK—C and Hek-mGAS (FIGS. 7B, 7C, 7F), HCT-116 (FIGS. 7D-7F) and KM (FIG. 7F) cell lines. FACS isolation of cells+ve for indicated proteins is shown in FIGS. 7B, D7, 7E. Sorted cells stained for ANXA2 are shown in FIG. 7C. % cells sorted for indicated proteins from different cell lines are shown in FIG. 7F.

FIGS. 8A-8D show that PG over-expression in HEK-mGAS cells increases tumorigenic and metastatic potential of the cells in vivo. FIG. 8A: HEK—C and HEK-mGAS cells were subdermally inoculated into the flank of the athymic nude mice. As can be seen, HEK-mGAS grew significantly larger tumors compared to the HEK—C control cells. FIG. 8B: Table is presented. Only 1 out 6 mice inoculated with HEK—C cells grew tumors whereas all 6 out 6 mice inoculated with HEK-mGAS cells grew as tumors. HCT-116, which is a human colorectal cancer cell line, was used as a positive control. FIG. 8C. HEK-mGAS cells were inoculated into the spleen of the nude mice. The spleen was removed 24 hours post inoculation. HEK-mGAS cells metastasized to the liver (right panel). The liver was removed and the metastatic growths visualized with the help of GFP labeled progastrin peptide which binds CS-ANXA2 on the tumor cells. The green patches in the liver shown on the left-hand panel are positive for the metastasized HEK-mGAS cells. FIG. 8D: HEK-mGAS cells induced to over-express luciferase were orthotopically inoculated into the cecum of the nude mice. The HEK-mGAS-luciferase cells metastasized to the liver (left panel). HEK-mGAS-luciferase cells were also inoculated subdermally as a control (right panel).

FIGS. 9A-9B show metastatic growth of HEK-mGAS in the lung (FIG. 9A) and liver (FIG. 9B), was visualized by H&E staining (as shown in the middle panels) and by IF staining, using anti-ANXA2 antibodies (lower-most panels). Note that the surrounding normal tissues were negative for ANXA2 staining, confirming overexpression of ANXA2 in the tumor cells, especially at the outer edges of the tumors and metastatic growths.

FIGS. 10A-10E: Expression of Stem Cell Markers in HCT-116 cells. FIG. 10A: Immunoblots demonstrating expression of DCAMKL-1, CD44 and LGR5 in HCT-116 cells. FIG. 10B: Cells positive for the markers ranged between 1-3% which is representative of cancer stem cell populations in a cell line. FIGS. 10C-10E: HCT-116 cells were FACSsorted for stem cell markers DCAMKL-1 (FIG. 10C), CD44 (FIG. 10D) and LGR5 (FIG. 10E).

FIG. 11 depicts the growth of tumorospheres from colon cancer cell lines. DLD-1, HT-29 and HCT-116 cells were grown as tumorospheres in low-attachment plates and imaged with a white light microscopy at 10× magnification. Cells were treated every 2-3 days with DMEM/F12, containing growth supplements.

FIG. 12 depicts HCT-116 cells enriched for specific stem cell populations by FACS and grown as tumorospheres. HCT-116 cells were enriched with either DCAMKL-1, CD44 or LGR5 by FACS analysis. Cells positive for the specific markers were then grown as tumorospheres for 10 days in low-attachment plates and imaged with a white light microscopy at 4× magnification.

FIG. 13 shows the differential localization of cancer stem cells, positive for DCAMKL-1, CD44 and LGR5, in the tumorospheres. HCT-116 cells were grown as tumorospheres. On day 10, tumorospheres were fixed with 10% formalin and store at 4° C. overnight. The following day, tumorospheres were transferred to an agar solution and processed for paraffin imbedding and sectioning. Immunofluorescence was performed on sections for the specific markers DCAMKL-1, CD44 and LGR5. DCAMKL-1 and LGR5 stained cells were present in the outer periphery of the spheres whereas CD44 cells were stained throughout the sphere. DAPI was used to stain the nucleus of the cells.

FIGS. 14A-14C show cells expressing CS-ANXA2 are also positive for stem cell markers. HEK-mGAS cells were FACSorted with AnnexinA2 Antibody. ANXA2+ and ANXA2-cells were cytospun onto glass slides and stained by immunofluorescence for AnnexinA2, DCAMKL, CD44 (FIGS. 14A-14B) and LGR5 (FIG. 14C).

FIGS. 15A-15C are a diagnostic scheme for isolating nucleated epithelial cells from the blood. FIG. 15A: Blood is collected into a lithium heparin tube and centrifuged at 1500 rpm (500 g) for 5 min. the supernatant (containing the white blood cells) was FACSorted using anti-CD45 antibodies, a marker for white blood cells. FACSorted CD45+ and CD45-cells were then cytospun and stained with anti-CD45-antibodies to confirm efficacy of the sorting method for depleting the blood of white blood cells (WBC). The pelleted cells containing red blood cells and nucleated epithelial cells were also FACSorted using anti-CD45 antibodies to eliminate any contamination of CD45 (WBC) positive cells. CD45-population was cytospun onto glass slides and stained by IF for DCAMKL-1, CD44 and LGR5. DAP1 was used to stain all nucleated cells which enabled us to differentiate between red blood cells and epithelial cells. FIG. 15B: % cells positive for the specific markers were analyzed in the blood of either normal nude mice (N) (which were not bearing any tumors), or from mice bearing primary subdermal xenografts tumors (PT) or mice bearing metastatic tumors (Met). The total number of circulating tumor stem cells/ml blood, positive for the 4 indicated markers, increased progressively from very low levels in mice with no tumors, to significant levels in mice with only primary tumors. The numbers of DCAMKL-1, Lgr5, CS-AnnexinA2 and CD44 positive CTCs were highest in mice bearing metastatic tumors. Interestingly the increase in CTCs positive for CS-AnnexinA2 staining was most significant in mice with metastatic tumors compared to mice with only primary tumors, suggesting that high numbers of CS-ANXA2 positive CTCs may be a selective marker for metastatic disease. The increase in the total numbers of LGR5 positive CTCS was also proportional to the status of the disease in the mice. C. Importantly, CTCs positive for CS-AnnexinA2 were also positive for the stem cell markers, DCAMKL-1 (FIG. 15C). These data show that CS-AnnexinA2 expression in CTCs may mark for cells which are highly metastatic, and thus positive selection of CTCs with CS-AnnexinA2 along with DCAMKL-1 or Lgr5, will likely provide the most accurate information regarding numbers of Circulating Tumor Stem Cells (CTSCs). Since CTSCs can seed and grow tumors at distant sites more potently than the generic CTCs, this assay will be superior to other assays currently available in the market.

FIG. 16 is a confirmation of depletion of WBC by the simple method described in FIG. 15A. Blood from patients or mice was fractionated as described in FIG. 15A. In the top panel, the supernatant containing CD45+ population was cytospun and stained for CD45 by IF to visualize the presence of white blood cells. In the lower panel, the CD45+ population from the pellet, which should be depleted of white blood cells, was cytospun and stained for CD45 by IF. Data reveals relative absence of CD45+ cells in the pellet confirming that this simple method of fractionation and FACS sorting effectively depleted the pelleted plasma sample of WBC.

FIGS. 22A-22E show measurements of ANXA2. FIGS. 22A-22: Standard curves (FIGS. 22B, 22D) of rhANXA2 by quantitative immunoblot analysis (FIGS. 22A, 22C) in 2 concentration ranges. FIG. 22E: Relative concentrations of ANXA2 in the conditioned medium (CM) of indicated cell lines measured by Immunoblot analysis as described in the text.

Figure 23A:
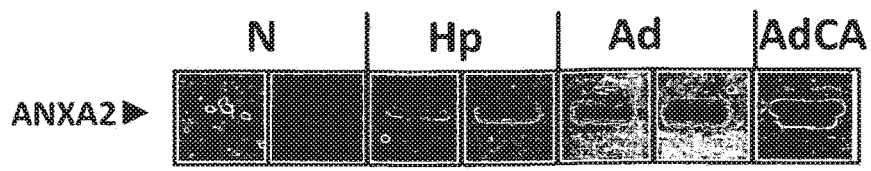
Figure 23B:
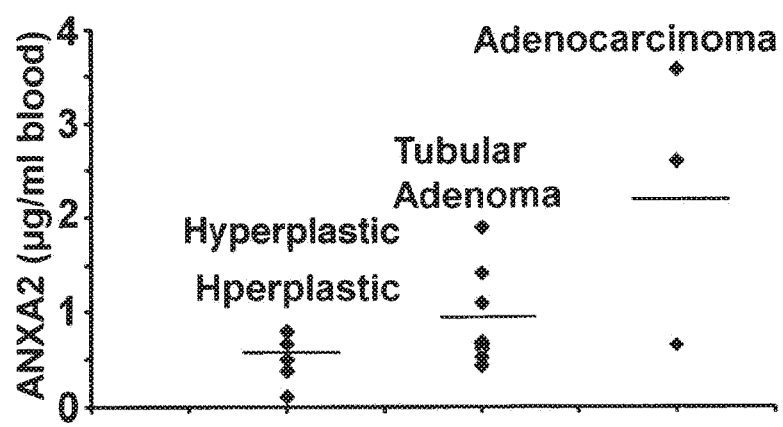
Figure 23C:
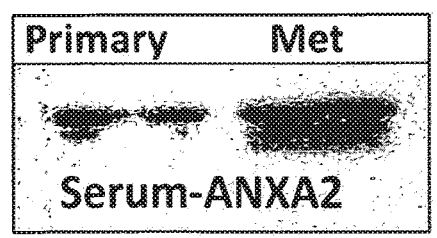
Figure 23D:
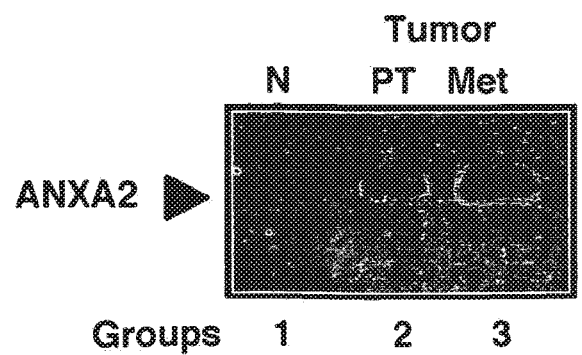

FIGS. 23A-23D show measurements of ANXA2 in humans. FIG. 23A: Relative levels of ANXA2 in the serum of either normal (N) patients or patients with benign precancerous growths (Hyperplastic growths, Hp; Adenomatous growths, Ads) or cancerous growths (Adenocarcinomas, AdCAs) in the colon. FIG. 23B: Scatter plot of ANXA2 concentrations measured in patients with the indicated growths is presented. FIGS. 23C-23D: Relative levels of serum ANXA2 in nude mice from two separate sets of experiments. Nude mice were either sham operated and served as control normal mice, or the nude mice were inoculated subdermally with cancer cells to grow primary xenografts tumors or were inoculated in the spleen to grow metastatic tumors. Control mice were negative for serum ANXA2. Control mice were negative for serum ANXA2 in both experiments. Mice with metastatic growths had 2-4 fold higher levels of serum annexinA2/ml blood compared to mice bearing only primary subdermal xenografts, indicating that presence of very high levels of serum annexinA2 may reflect the presence of advanced metastatic cancers.

Figure 24:
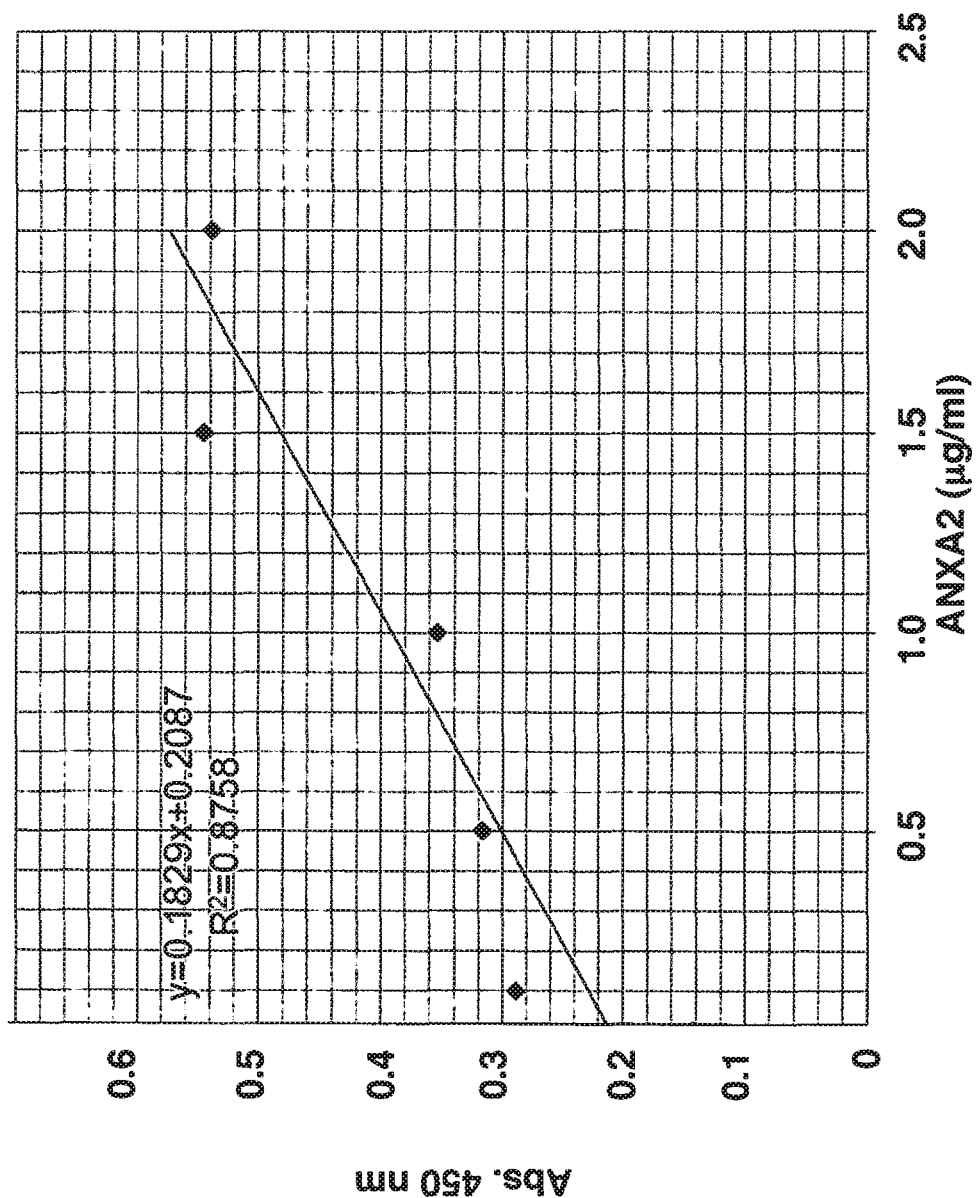

FIG. 24 shows the results of an Elisa assay using non-immune human serum, spiked with increasing concentrations of rhANXA2. Polyclonal Ab against ANXA2 was coated at a dilution of 1:500 at 4° C. overnight. The wells were then washed off to remove excess ANXA2 and incubated with serum samples spiked with ANXA2 at various concentrations for 2 h at room temperature. The unbound ANXA2 in the serum samples were washed off and the plates incubated with Mab against ANXA2 for 1.5 h. Bound Ab was detected by incubation with Anti-mouse-HRP Ab at a dilution of 1:1000 for 1 h at RT followed by washing and color development by TMB reagent. Human serum from patients was diluted 1:20 before processing as described for standards.

DETAILED DESCRIPTION OF THE INVENTION

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); Sambrook, et al., Molecular Cloning: A Laboratory Manual (2nd Edition, 1989); Handbook of Surface and Colloidal Chemistry (Birdi, K. S. ed., CRC Press, 1997); Short Protocols in Molecular Biology, 4th ed. (Ausubel et al. eds., 1999, John Wiley & Sons); Molecular Biology Techniques: An Intensive Laboratory Course (Ream et al., eds., 1998, Academic Press); PCR (Introduction to Biotechniques Series), 2nd ed. (Newton & Graham eds., 1997, Springer Verlag); Peters and Dalrymple, Fields Virology, 2nd ed., Fields et al. (eds.) (B.N. Raven Press, New York, N.Y.). All publications, patents and patent applications cited herein, whether supra or infra, are hereby incorporated by reference in their entirety.

As used herein the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "subject" or individual refers to any target of the treatment. Preferably, the subject is a mammal, more preferably, the subject is a human.

It is further to be understood that all base sizes or amino acid sizes, and all molecular weight or molecular mass values, given for nucleic acids or polypeptides are approximate, and are provided for description.

Although methods and materials similar or equivalents to those described herein can be used in the practice or testing of the present disclosure, suitable methods and materials are described below. In case of conflict, the present specification, including explanations of terms, will control. In addition, the materials, methods, and examples are illustrative only and not intended to be limiting. Furthermore, unless otherwise required by context, singular terms shall include pluralities and plural terms shall include the singular.

In one embodiment of the present invention, there is provided a method of distinguishing an individual who may be positive for the presence of pre-cancerous, benign tumorous growths (such as colonic polyps), from a subject who is free of any benign or cancerous tumorous growths, as a screening procedure, comprising the step of measuring the amount of AnnexinA2 in the blood or serum of said subject.

In another embodiment of the present invention, there is provided a method of distinguishing a subject who may be positive for either early stage (primary) cancerous growths or late stage (metastatic) cancer growths, comprising the step of measuring the amount of AnnexinA2 in the blood or serum of said subject. AnnexinA2 may be measured by a technique known to a person having ordinary skill in this art, such as for example but not limited to, an anti-ANXA2 antibody. Preferably, the anti-ANXA2 antibody is anti-ANXA2 antibody IgG.

In another embodiment of the present invention, there is provided a method of identifying whether a subject is positive for metastatic cancerous growths or relapse of the cancer disease, post-treatment, comprising the step of measuring circulating metastatic tumor stem cells in blood or plasma of said subject. Generally, invasive/metastatic circulating tumor cells are positive for membrane-associated ANXA2 (CS-ANXA2).

It is contemplated that the sensitivity or accuracy of the CTC assay is enhanced by combining negative selection with positive selection using antibodies against newly identified proteins, as described below. It is envisioned that this method could be useful in diagnosing the presence of any epithelial cancer at different stages of the disease, and will be specially applicable to identifying the presence of colorectal cancers at different stages of the disease, as well as pancreatic, ovarian, renal and epithelial cancers. The presence of circulating metastatic tumor stem cells in the blood or plasma of the subject is identified by measuring the presence of CS-ANXA2 and DCAML-1 or Lgr5 positive circulating tumor stem cells, which is diagnostic/prognostic for the presence of metastatic cancerous tumors.

In one aspect, the cancer is a recurrence of cancer, post-treatment. CS-ANXA2+DCAMKL-1 or Lgr5 may be measured with any technique known in the art although measurement with an antibody is preferred. Representative antibodies include but are not limited to anti-ANXA2 IgG antibody, anti-DCAMKL IgG antibody or an anti-Lgr5 IgG antibody. In a most preferred aspect of this method, the cancer is colorectal but the method may also be applied to colorectal, pancreatic, ovarian, renal and epithelial cancers.

The following examples are given for the purpose of illustrating various embodiments of the invention and are not meant to limit the present invention in any fashion.

Example 1

Autocrine and Endocrine Growth Factors Mediate Tumorigenic Effects on Epithelial Cells by Binding Cell-Surface Associated AnnexinA2 (CS-ANXA2)

Figure 1A:
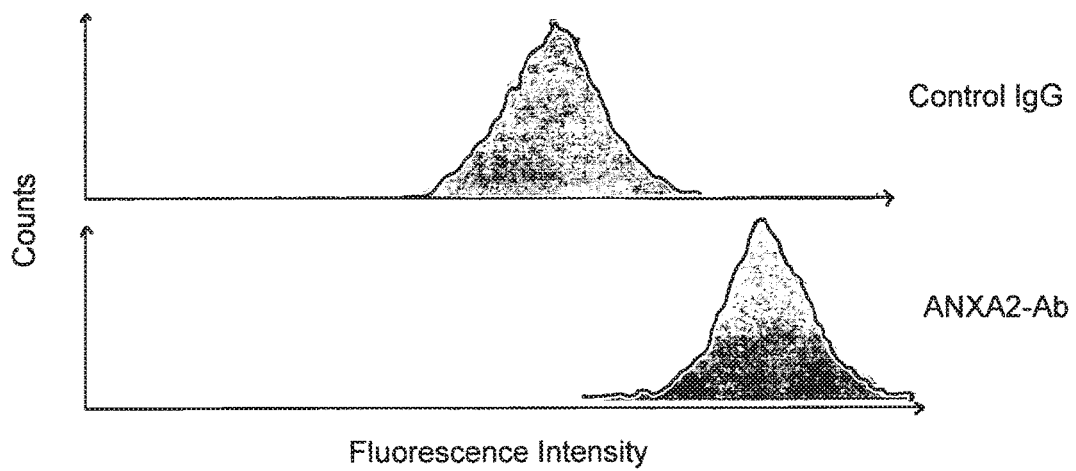
Figure 1B:
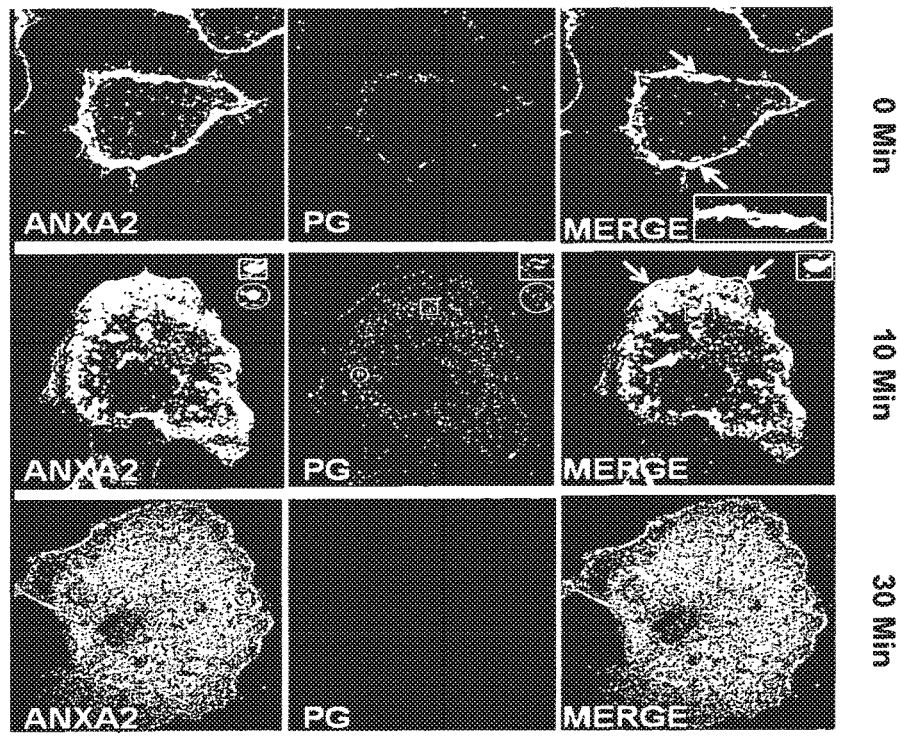
Figure 2A:
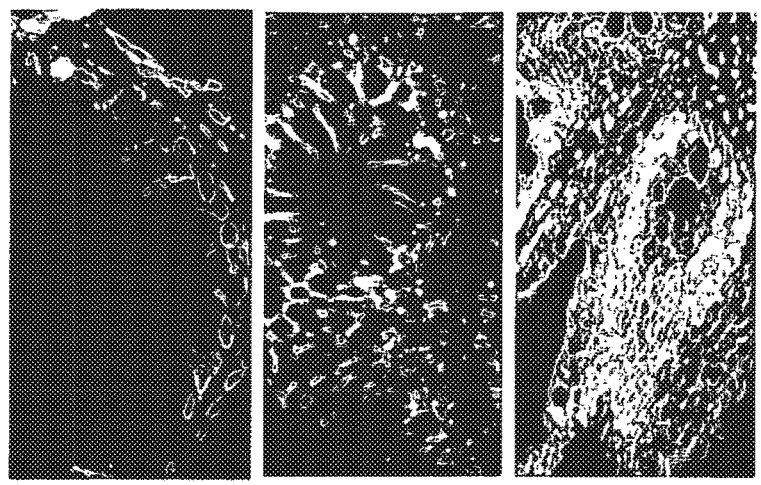
Figure 2B:
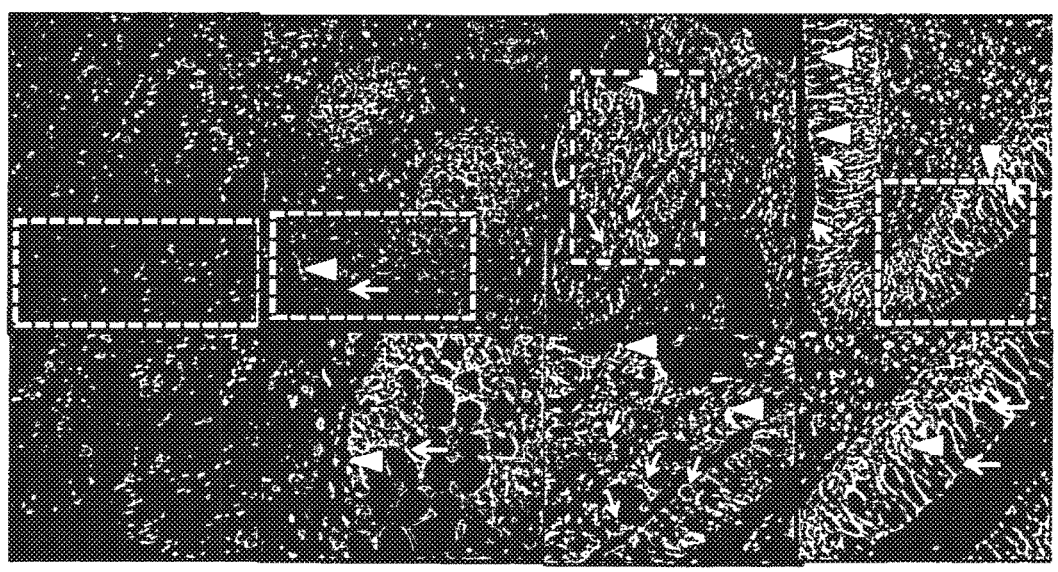

Non-amidated precursor forms of gastrins, called progastrin peptides (PG), are potent mitogens, and exert proliferative/anti-apoptotic/co-carcinogenic and tumorigenic effects on normal and cancerous intestinal, pancreatic and lung epithelial cells (22-29). Cell surface associated ANXA2 (CS-ANXA2) functions as a high affinity, non-conventional receptor protein for PG peptides (30), and is required for mediating the growth promoting effects of PG on epithelial cells from the intestine, embryonic kidney and pancreatic cancers, in vitro (27,30) and in vivo (31). Data demonstrating the presence of CS-ANXA2 on intestinal epithelial cells is presented in FIGS. 1A-1B. The fluorescence intensity of cells labeled with anti-ANXA2-antibodies (Abs) was increased >10-fold compared to cells labeled with control IgG (FIG. 1A), confirming the presence of CS-ANXA2 on intestinal epithelial cells (IEC-18) (32). CS-ANXA2 was reported on embryonic kidney epithelial cells (31) which respond to growth promoting and tumorigenic effects of PG peptides (33). When target cells such as intestinal epithelial cells are stimulated with PG, at initial time points of 0 min, the PG peptide is tightly associated with CS-ANXA2 (FIG. 1B, upper panel), followed by rapid internalization of PG/ANXA2 complexes via the endocytotic pathway into early endosomes (FIG. 1B, middle panel) (34). However, by 30 min the internalized progastrin peptide is completely degraded (FIG. 1B, lower panel). Endocytotic internalization of PG/ANXA2 complexes is required for mediating signaling and growth effects of PG (34). Similarly, internalization of PG/ANXA2 complexes was also measured in transformed epithelial cells (31). In order to examine a physiological and pathological relevance of these findings, additional studies were conducted with tissue samples from patients positive for colonic adenomas and colonic adenocarcinomas. Paraffin-embedded sections from representative patient samples of normal colons, benign colonic adenomas (Ad) and cancerous colonic adenocarcinomas (AdCA) were processed for immunoflouroscense (IF) staining with anti-ANXA2-IgG and DAP1 (for nuclear staining), as shown in FIG. 2A. Normal colonic samples were poorly stained for ANXA2, while adenomas and adenocarcinomas are increasingly stained with ANXA2, confirming that ANXA2 expression is significantly increased during colon carcinogenesis. Gastrin gene and progastrin expression has also been similarly demonstrated to be significantly increased during colon carcinogenesis (26), and PG peptide strongly co-localized with ANXA2 in the colonic adenoma and adenocarcinoma samples from patients (FIG. 2B). These studies thus confirm the presence of cell surface associated ANXA2 (CS-ANXA2) on colonic tumor cells, which appear to correlate with the stage of the disease.

Example 2

Figure 3A:
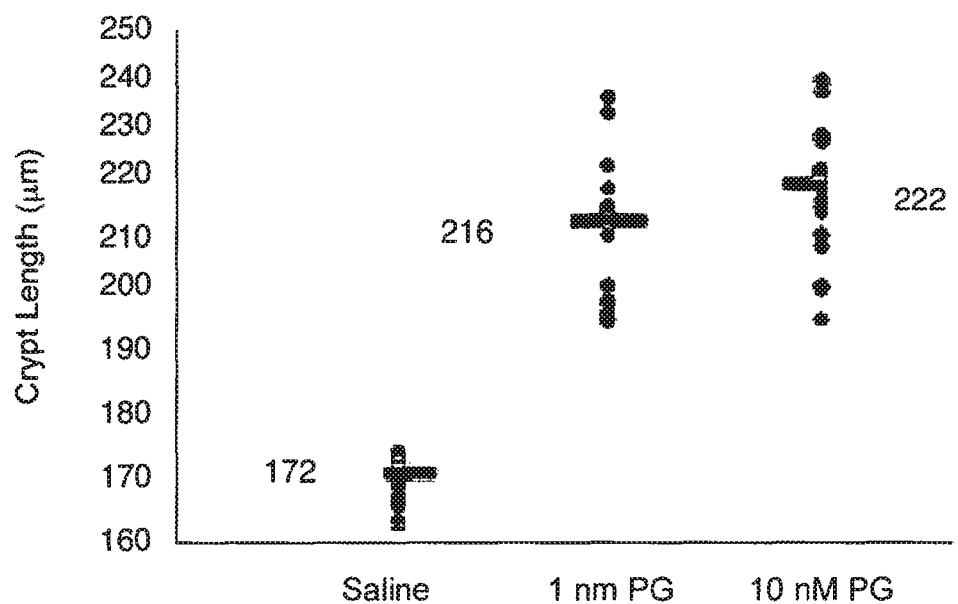
Figure 3B:
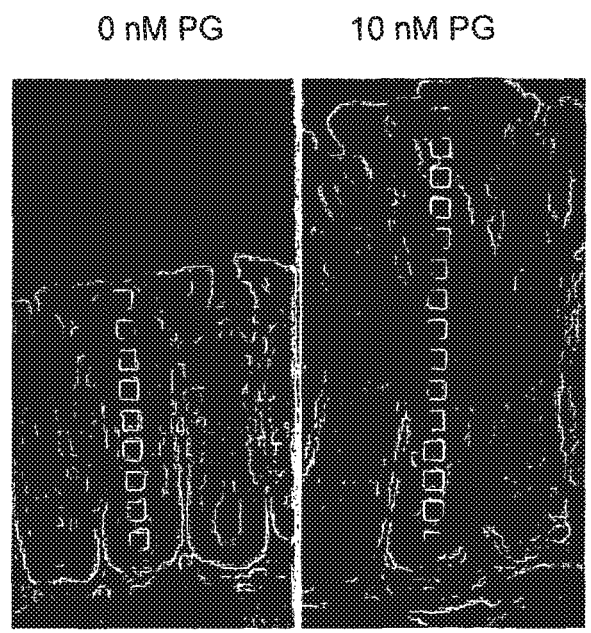
Figure 3C:
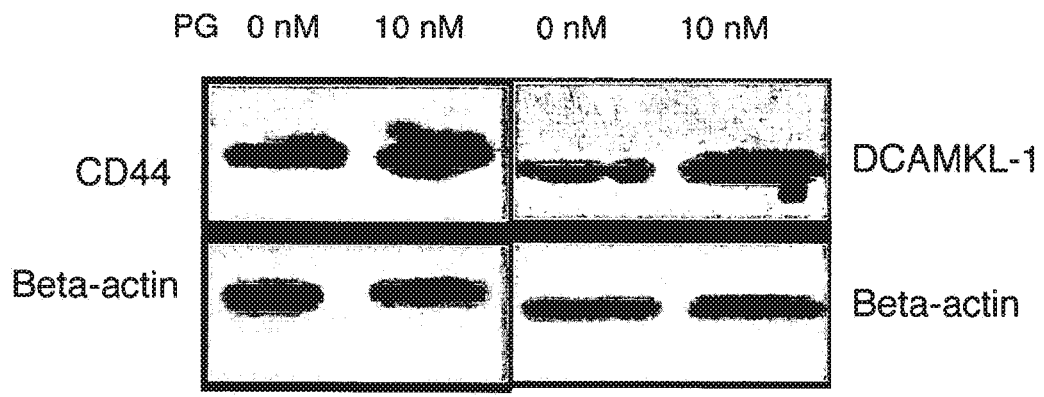
Figure 3D:
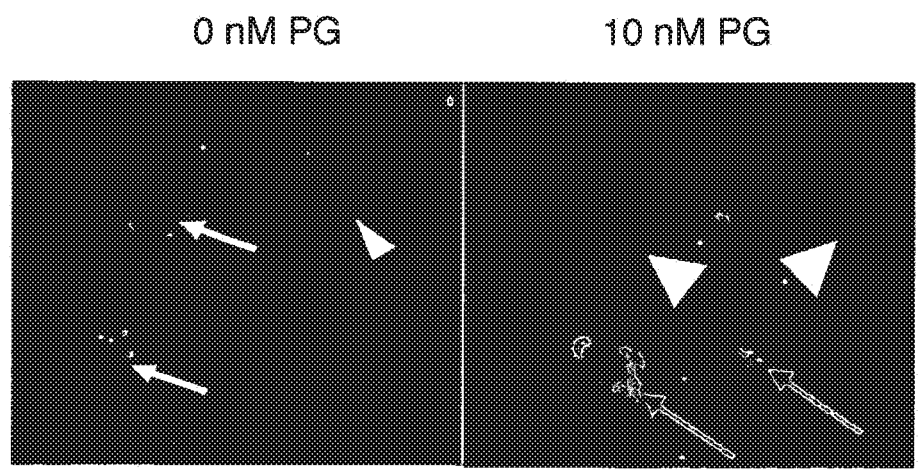
Figure 4A:
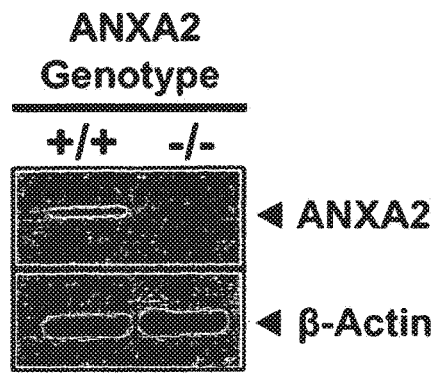
Figure 4B:
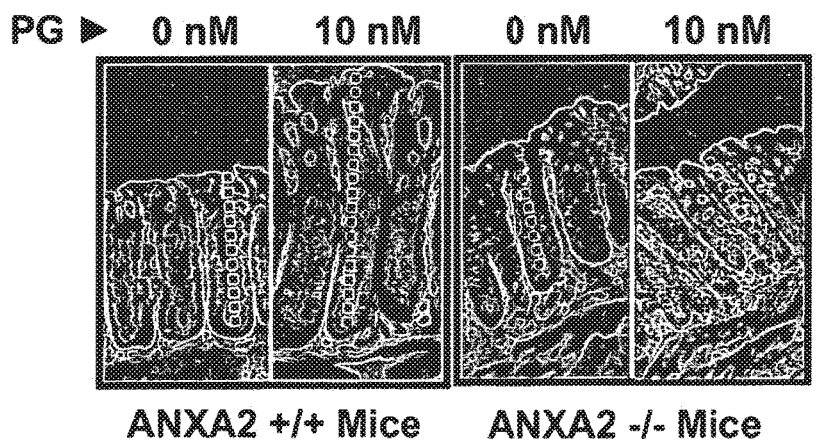
Figure 4C:
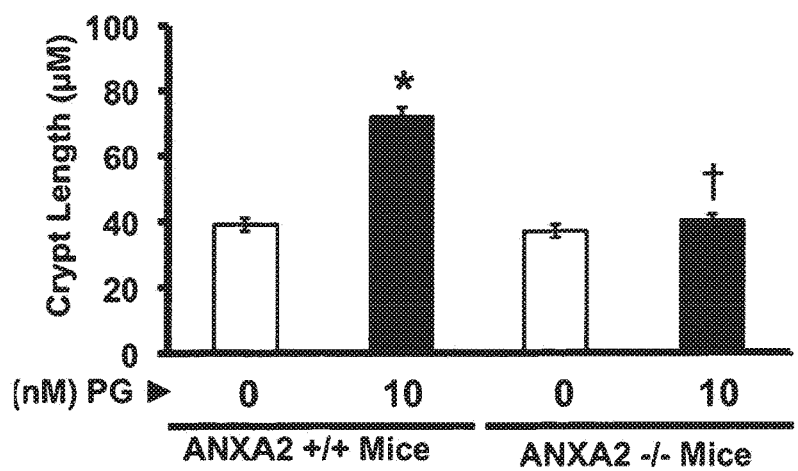

AnnexinA2 Expression is Required for Measuring an Increase in Stem Cell Populations The proliferative and tumorigenic effects of PG peptides are associated with the significant increase in the stem cell populations within colonic crypts of mice (31). A significant increase in the length of the colonic crypts in response to 1-10 nM PG was confirmed in C57Bl/J6 mice (FIGS. 3A-3B), as reported with transgenic FVB/N mice (25). The concentrations of stem cell markers, CD44 and DCAMKL-1 were significantly increased in colonic crypts of mice treated with 10 nM PG (FIG. 3C), and the total number of cells positive for CD44 and DCAMKL+1 markers were also significantly increased in the colonic crypts of PG-treated mice (FIG. 3D). ANXA2 knockout (ANXA2$^{-/-}$) mice were used to examine if ANXA2 expression was required for mediating the proliferative effects of PG on the colonic crypts of mice. The ANXA2$^{-/-}$ mice were confirmed by Western Blot analysis (FIG. 4A). Unlike the wild type ANXA2$^{+/+}$ mice, the ANXA2$^{-/-}$ mice were non-responsive to the growth promoting effects of PG (FIGS. 4B-4C).

Figure 4D:
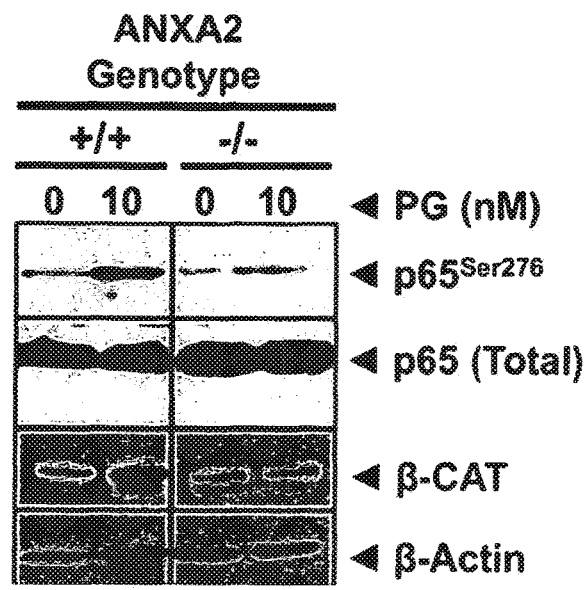
Figure 4E:
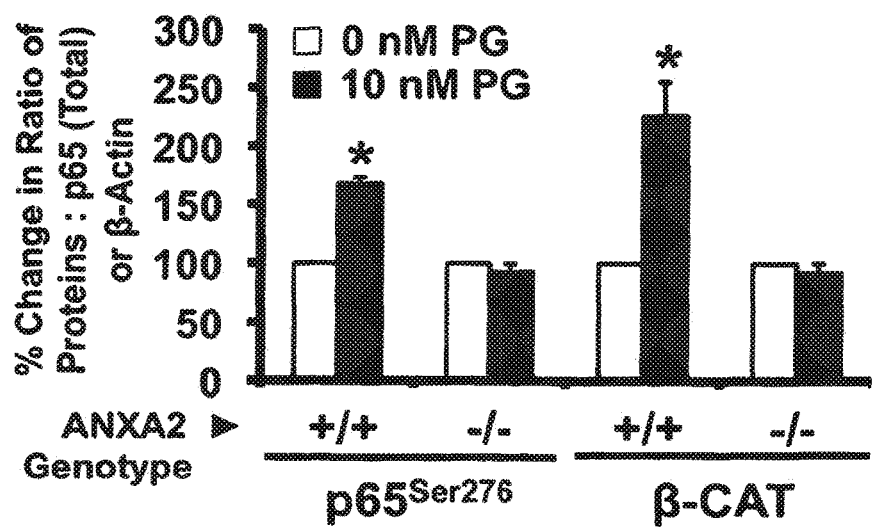
Figure 5A:
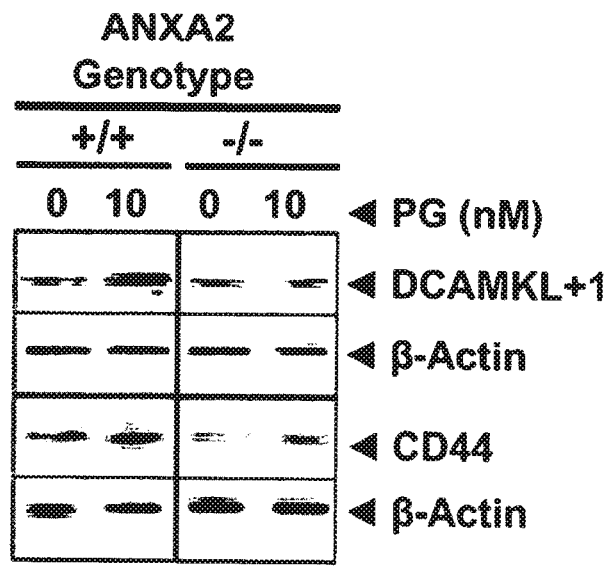
Figure 5B:
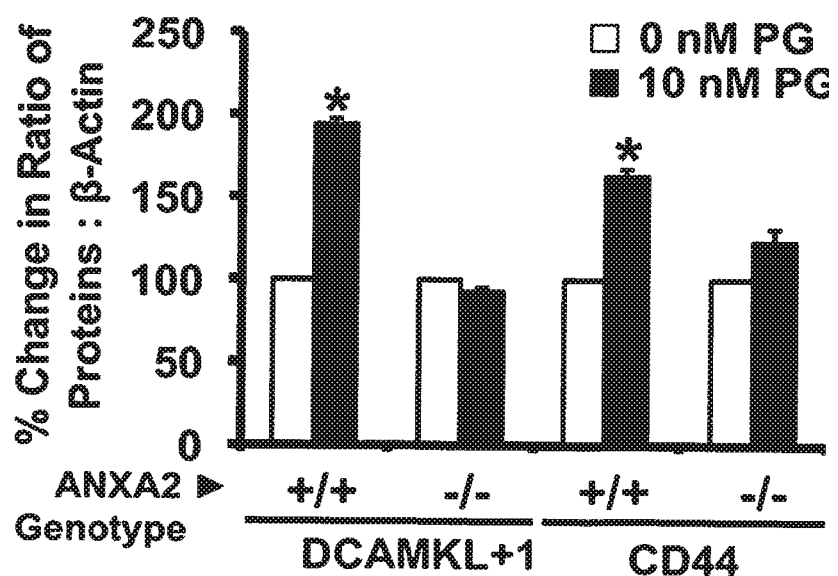
Figure 5C:
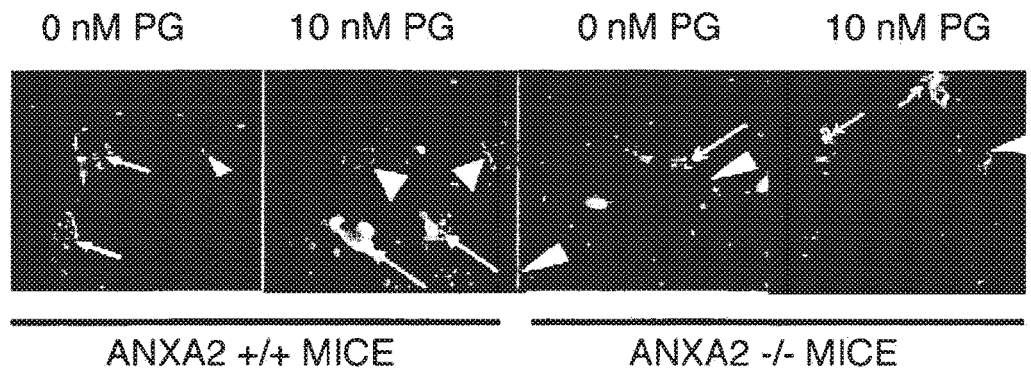
Figure 5D:
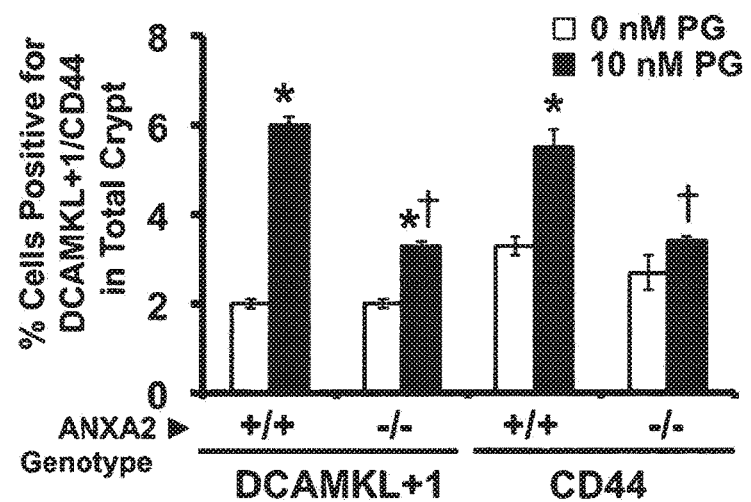

Two strong transcriptional factors, NFκB and β-catenin are significantly up-regulated in response to PG stimulation in vitro and in vivo (23,27,36), and using the ANXA2$^{-/-}$ mice in the absence of ANXA2 expression, NFκB (p65$^{se276}$) and β-catenin (β-cat) were not up-regulated in response to PG (FIGS. 4D-4E) (31). Similarly ANXA2 expression was required for mediating the effects of PG peptides on stem cell populations (31). Both the concentration (FIGS. 5A-5B) and total number of cells (FIGS. 5C-5D) positive for the stem cell markers DCAMKL+1 and CD44 failed to be up-regulated in response to PG in mice knocked down for the expression of ANXA2, while the wild type ANXA2 expressing mice (ANXA2$^{+/+}$) were strongly up-regulated for stem cell populations in response to PG stimulation (31).

Example 3

Figure 6A:
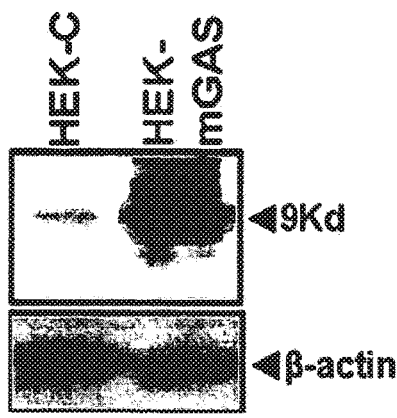
Figure 6B:
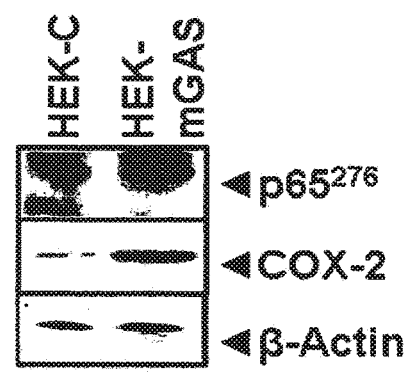
Figure 6C:
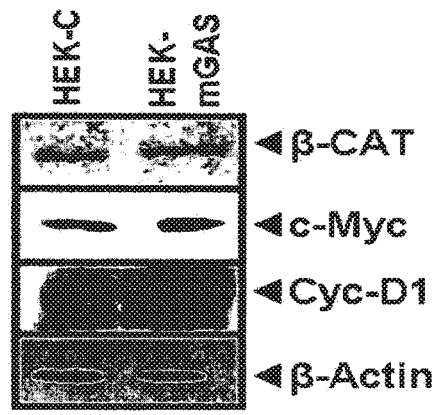
Figure 6D:
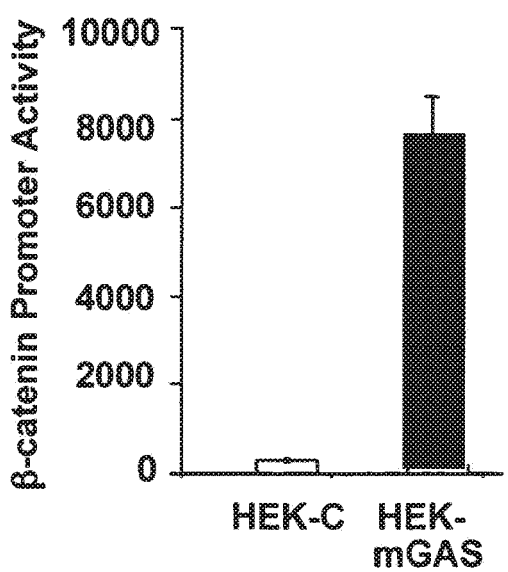
Figure 6E:
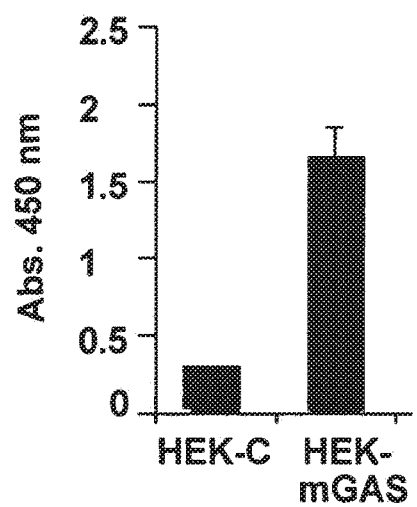
Figure 6F:
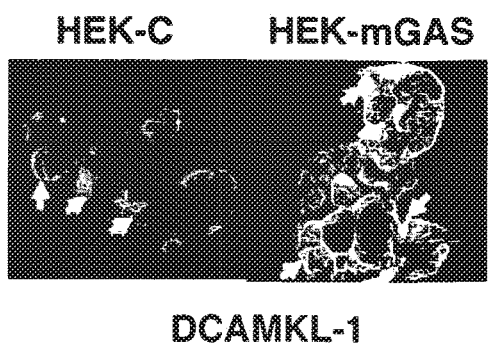
Figure 6I:
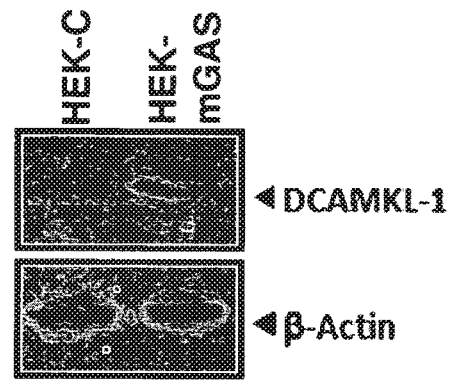
Figure 6G:
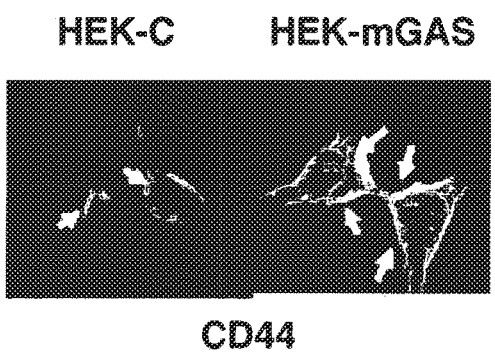
Figure 6J:
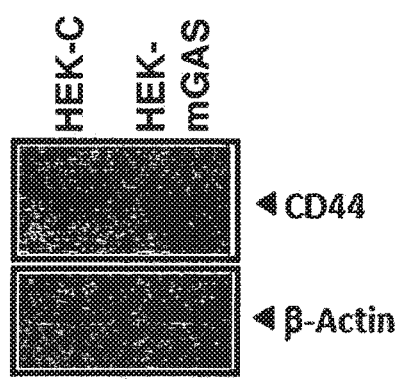
Figure 6H:
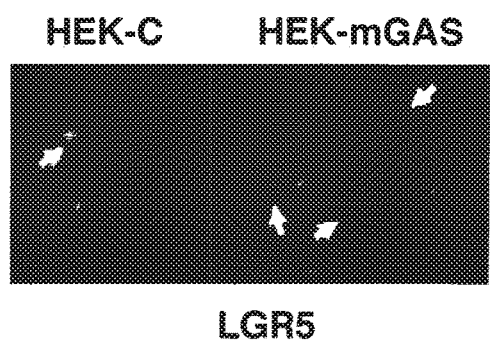
Figure 6K:
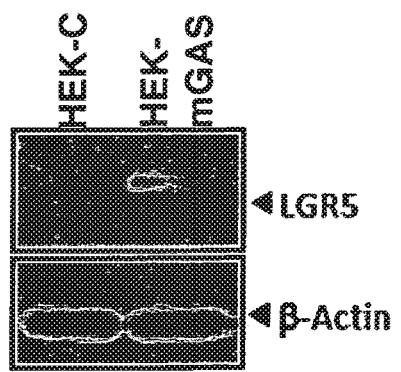

Tumorigenic Transformation of Kidney Epithelial Cells by Over-Expression of PG, is Associated with Significant Up-Regulation of ANXA2 and Stem Cell Marker Proteins In order to further examine the tumorigenic and co-carcinogenic effects of PG/ANXA2, non-transformed embryonic kidney epithelial cells (HEK-293) were used since these cells are very easy to clone and are responsive to growth effects of PG peptides. Clones of HEK-293 cells were generated which either expressed the control vector (HEK—C) or the human gastrin gene vector (HEK-mGAS). The clones over-expressing gastrin gene were confirmed to be over-expressing the PG peptide (9Kd) (FIG. 6A). Over-expression of PG in HEK-293 cells induced activation of NFκB and β-catenin pathways (including p65$^{ser276}$, COX-II, β-catenin, c-Myc, cyclin D1) (FIGS. 6B-6E) (31). Over-expression of PG in HEK-293 cells also up-regulated the expression of stem cell markers DCAMKL-1, CD44 and Lgr5 in the HEK-mGAS vs the HEK—C cells as shown in FIGS. 6F-6K (31). ANXA2 expression levels were also significantly increased in HEK-mGAS vs HEK—C cells (FIG. 7A).

Figure 7A:
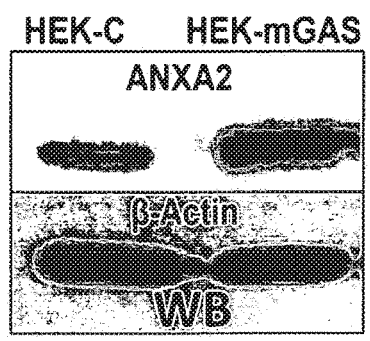
Figure 7B:
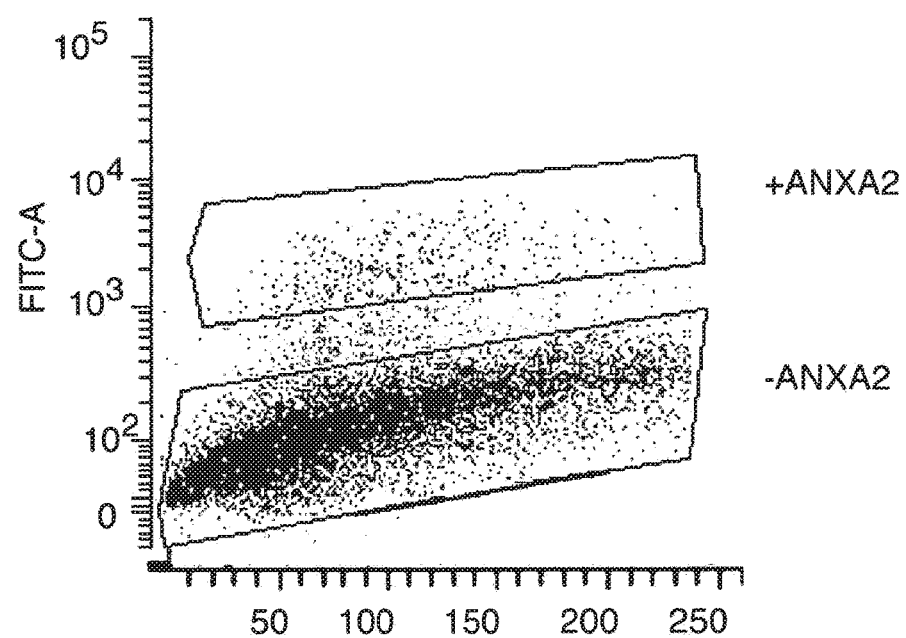
Figure 7C:
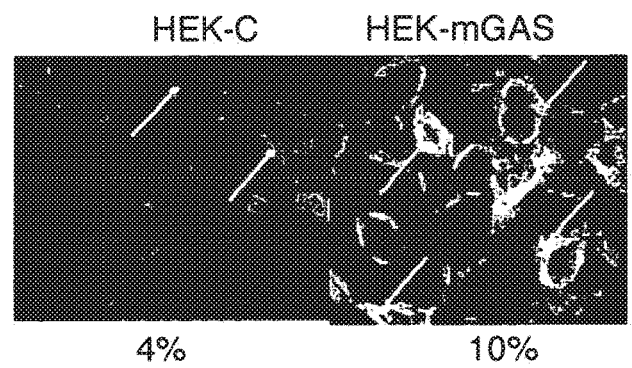

In the next set of studies, HEK—C and HEK-mGAS cells were FACSorted for enriching cell populations expressing either cell surface associated ANXA2 (FIGS. 7B-7C) or cell populations enriched in the expression of the extracellular domain of stem cell markers DCAMKL-1 and Lgr5 (FIGS. 7D-7E). Several colon cancer cell lines were similarly FACSorted and the % cells positive for ANXA2, DCAMKL and Lgr5 in the different cell lines is presented in FIG. 7F. As can be seen from the data presented in FIGS. 7A-7F, over-expression of autocrine growth factors in HEK-mGAS cells resulted in a significant up-regulation in the cell populations positive for not only ANXA2 but also stem cell markers DCAMKL and Lgr5. Surprisingly the colon cancer cell line HCT-116 which is known to express autocrine PG, albeit at much lower levels than the HEK-mGAS cells, had significantly lower % of cells that were positive for the indicated stem cell markers. KM12L4 cells are highly metastatic while KM12C colon cancer cells are not as metastatic, and once again there were some differences in the % cells that were positive for ANXA2, suggesting that cell surface expression of ANXA2 and other stem cell markers may be required for imparting a metastatic potential to these cells. In order to confirm this possibility, an athymic nude mice xenograft assay, as published (37,38), was used for examining the tumorigenic and metastatic potential of HEK-mGAS cells which were not only over-expressing progastrin peptides but also over-expressing ANXA2 and other stem cell markers (FIGS. 6A-6K and 7A-7F). Athymic nude mice were inoculated subdermally, on either side of the flank, with equal number of HEK—C, HEK-mGAS and HCT-116 (colon cancer cell line).

Figure 9B:
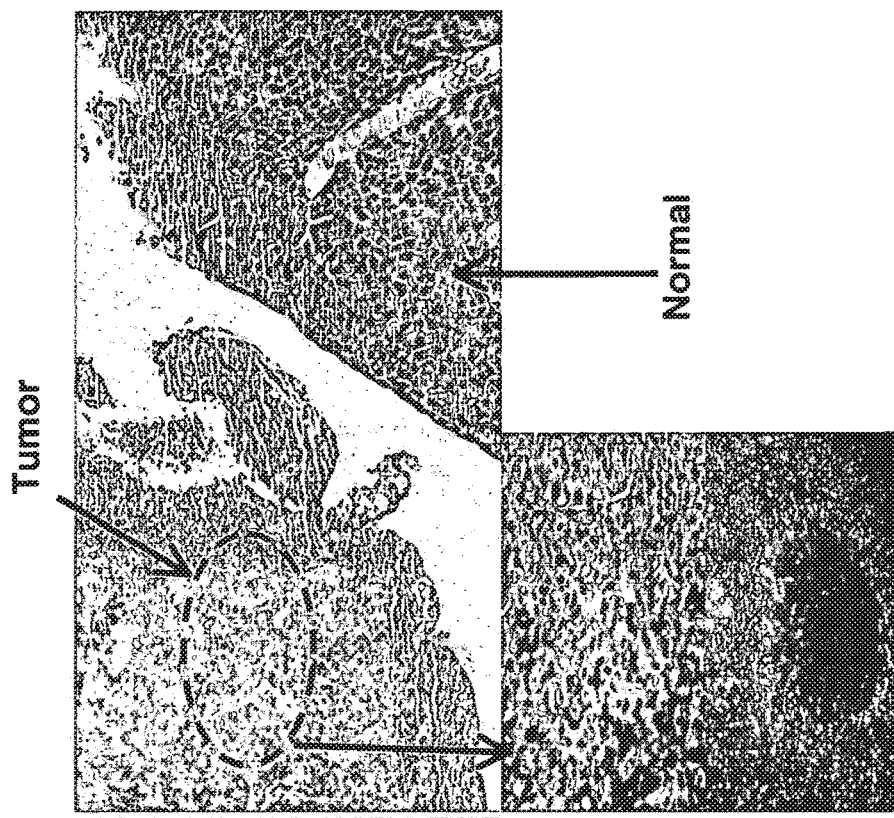
Figure 9A:
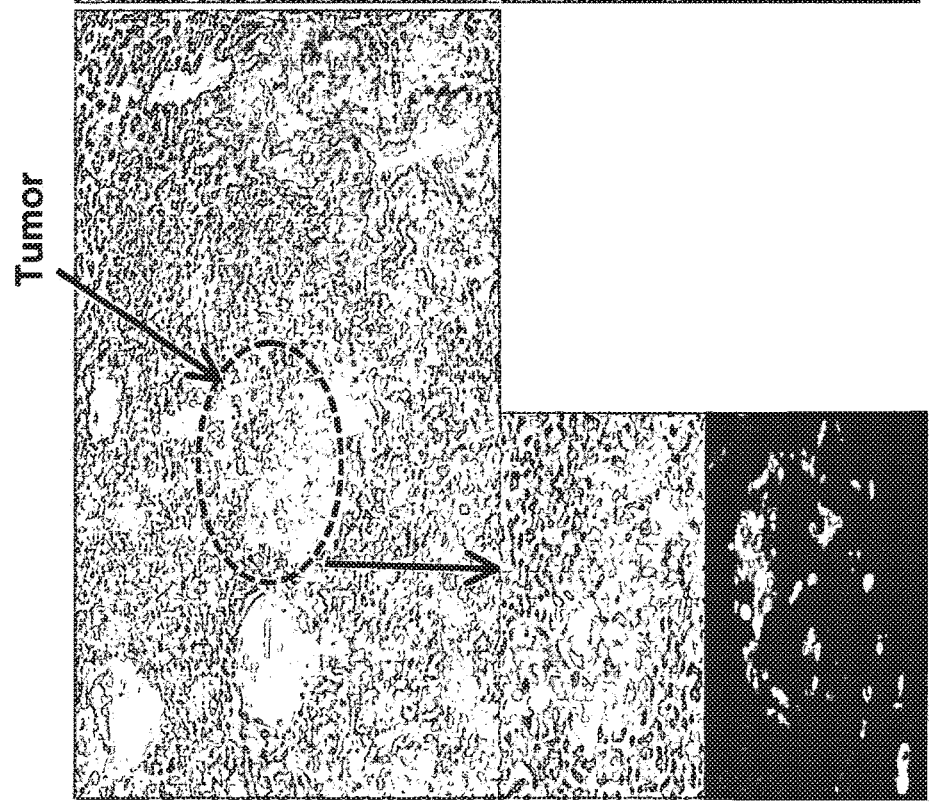
Figure 10A:
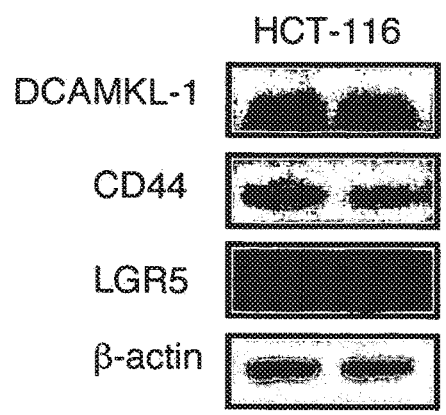
Figure 10B:
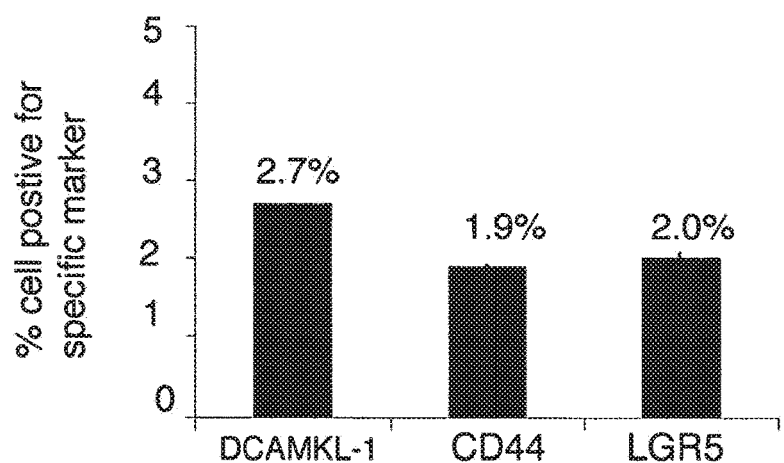
Figure 10C:
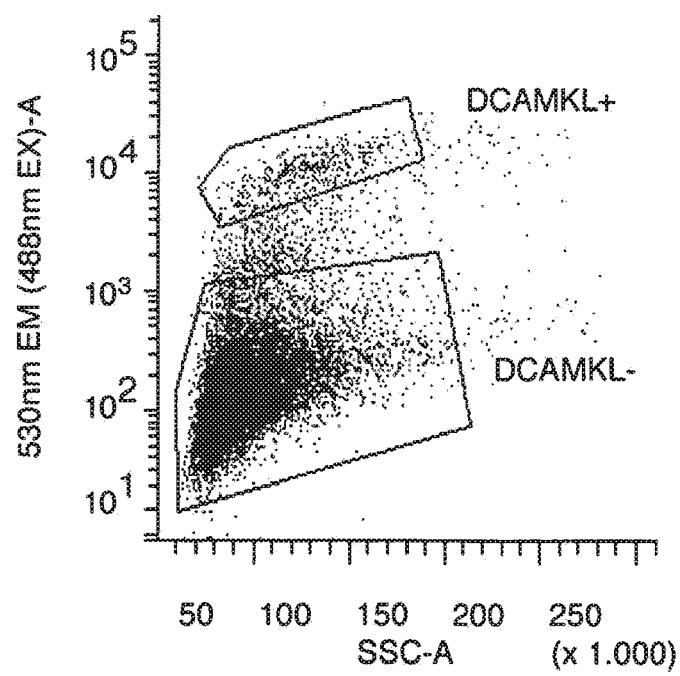
Figure 10D:
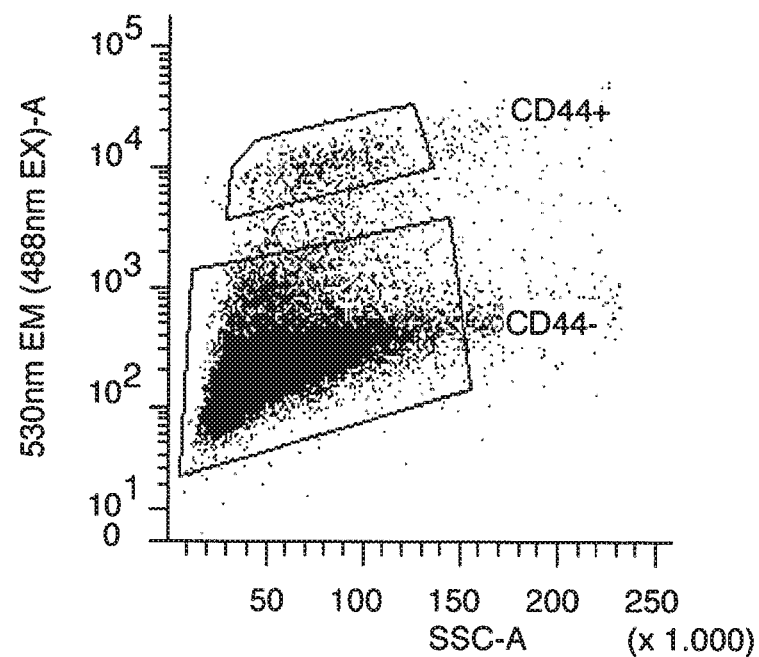
Figure 10E:
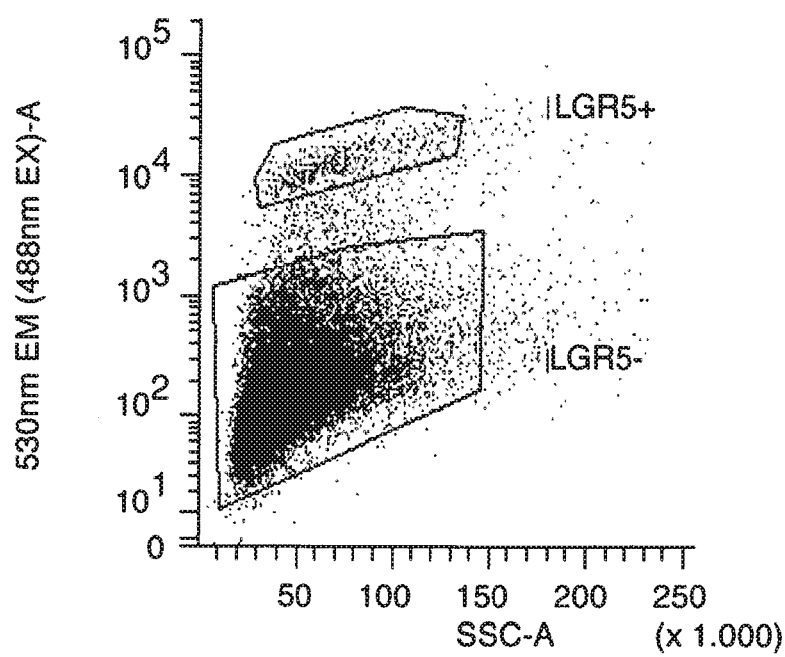

Representative tumor growths from mice inoculated with HEK—C and HEK-mGAS cells are shown in FIG. 8A. Majority of the mice inoculated with HEK—C cells did not grow tumors, and only 1 out of 6 tumors developed in these mice (FIG. 8B). On the other hand, all the mice inoculated with either HEK-mGAS or HCT-116 cells developed tumors of almost equivalent size (FIG. 8B). These data confirmed that over-expression of PG/ANXA2 and stem cell markers in HEK-mGAS cells may have imparted a tumorigenic potential to these cells (33). Two other models were used to confirm these findings wherein cells were inoculated either in the spleen (FIG. 8C) to develop metastatic tumors or were inoculated orthotopically in the cecum, which can also result in metastasis to the liver (FIG. 8D). HEK-mGAS cells over-expressing PG and ANXA2 formed distinct metastatic tumors in the liver and the lung (FIGS. 8C-8D, FIGS. 9A-9B). The metastatic growths in the liver were further confirmed by using GFP-labeled PG, which specifically binds cell surface associated ANXA2 present in the liver mets (right hand panel in FIG. 8C) (33). Thus, the outer edges of the metastatic tumors express elevated levels of CS-ANXA2 and potentially represent the highly metastatic component of the cancer cell populations. The latter possibility was further confirmed by staining paraffin-embedded sections of lung and liver tissues from the mice that had been inoculated with intrasplenic HEK-mGAS cells, which visually contained the metastatic masses (FIGS. 9A-9B). Both the lung and the liver metastatic tumor masses were once again positive for ANXA2 in circular pockets suggesting that the highly metastatic population may be growing outwards towards the edges of these tumors. Thus, the presence of CS-ANXA2 on cancer cells likely marks a highly metastatic population of cells and is a useful marker for detecting circulating cancer cells which are in the process of invading and migrating to distant sites for seeding metastatic tumors. Mice were also inoculated with HEK-mGAS cells which were engineered to over-express the luciferase vector downstream of a lentiviral vector, so that the growth of these tumors could be monitored in vivo using a bioluminescence machine, as shown in FIG. 8D. Within one month of inoculating the cecum of the mice one could observe the presence of metastatic growths along with the primary growths in the cecum of these mice (FIG. 8D). Thus the importance of CS-ANXA2 and stem cell marker proteins (DCAMKL/Lgr5) in the tumorigenic and metastatic potential of transformed and cancer cells is demonstrated.

Example 4

Stem Cell Populations in Colon Cancer Cells

A hallmark of cancer stem cells is the ability to give rise to rapidly proliferating progenitor cells which can either differentiate or continue to proliferate. The cancer stem cells are believed to divide asymmetrically and give rise to a daughter progenitor cell and a quiescent cancer stem cell in order to continue to provide the seed for the growth of tumors. The cancer stem cell population may thus either continue to divide asymmetrically or become quiescent like a dormant seed which can be revived to form tumors. Thus the presence of cancer stem cell populations can represent a major challenge for treatment purposes.

Several stem cell markers have been described (39-50), which likely mark both the quiescent and actively proliferating cancer stem cell populations. The markers DCAMKL-1, CD44 and Lgr5 were used for examining the stem cell populations in colon cancer cells (51).

Figures 11, 12:
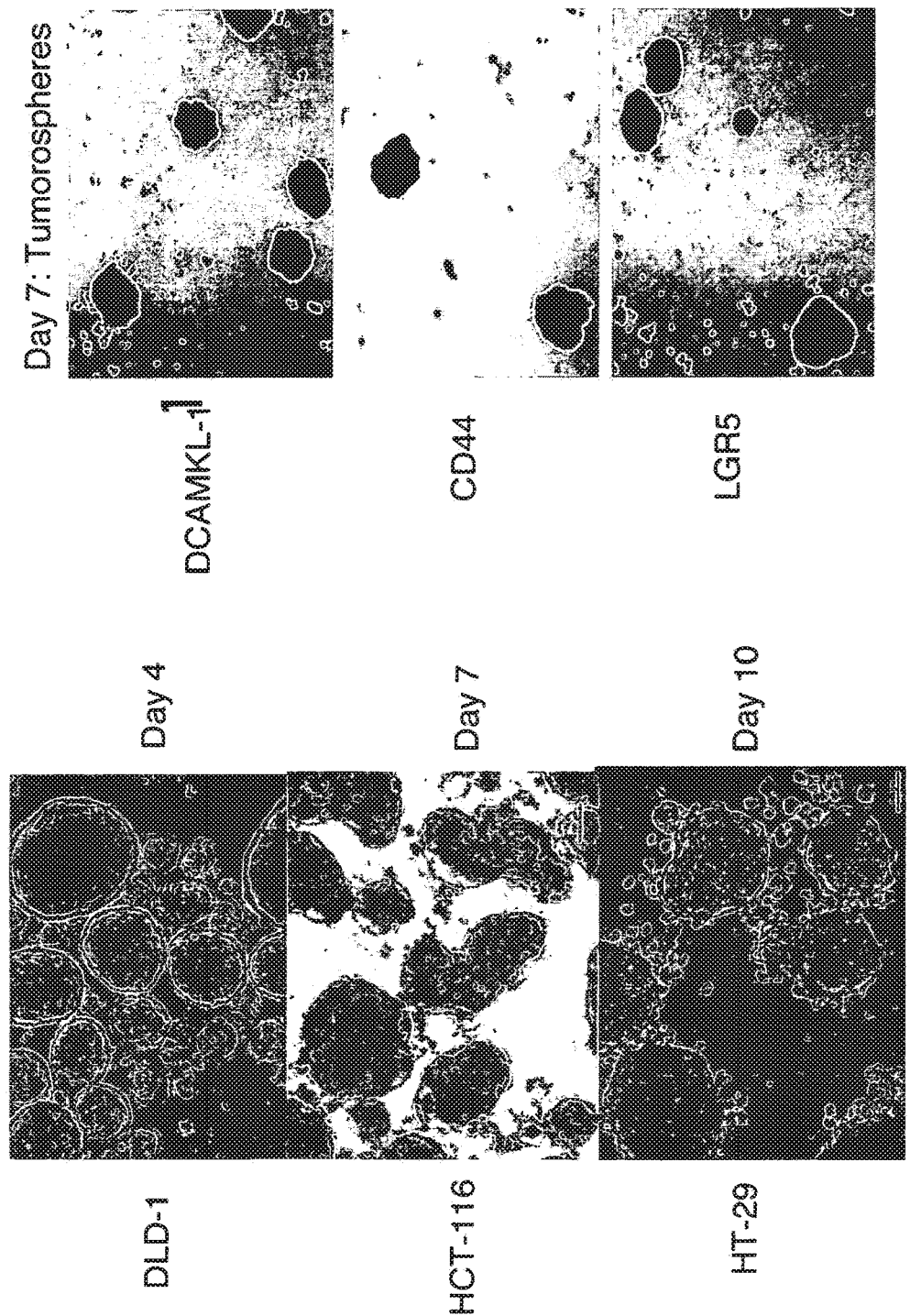

A very small % of cells (~1-3%) are positive for DCAMKL-1, CD44 and Lgr5 as shown in FIGS. 10A-10E. Stem cells have the unique feature and ability to grow as tumorospheres in non-adherent cell culture conditions in the presence of specific growth factors (46). The tumorosphere bioassay method was used for enriching stem cell populations from several colon cancer cell lines and representative data are presented in FIG. 11. As can be seen, spheres of many different sizes can grow with a distinct perimeter around them using the tumorosphere method. Depending on the population of cancer stem cells, different cell lines can form these spheres at different rates as shown in FIG. 11.

Figure 13:
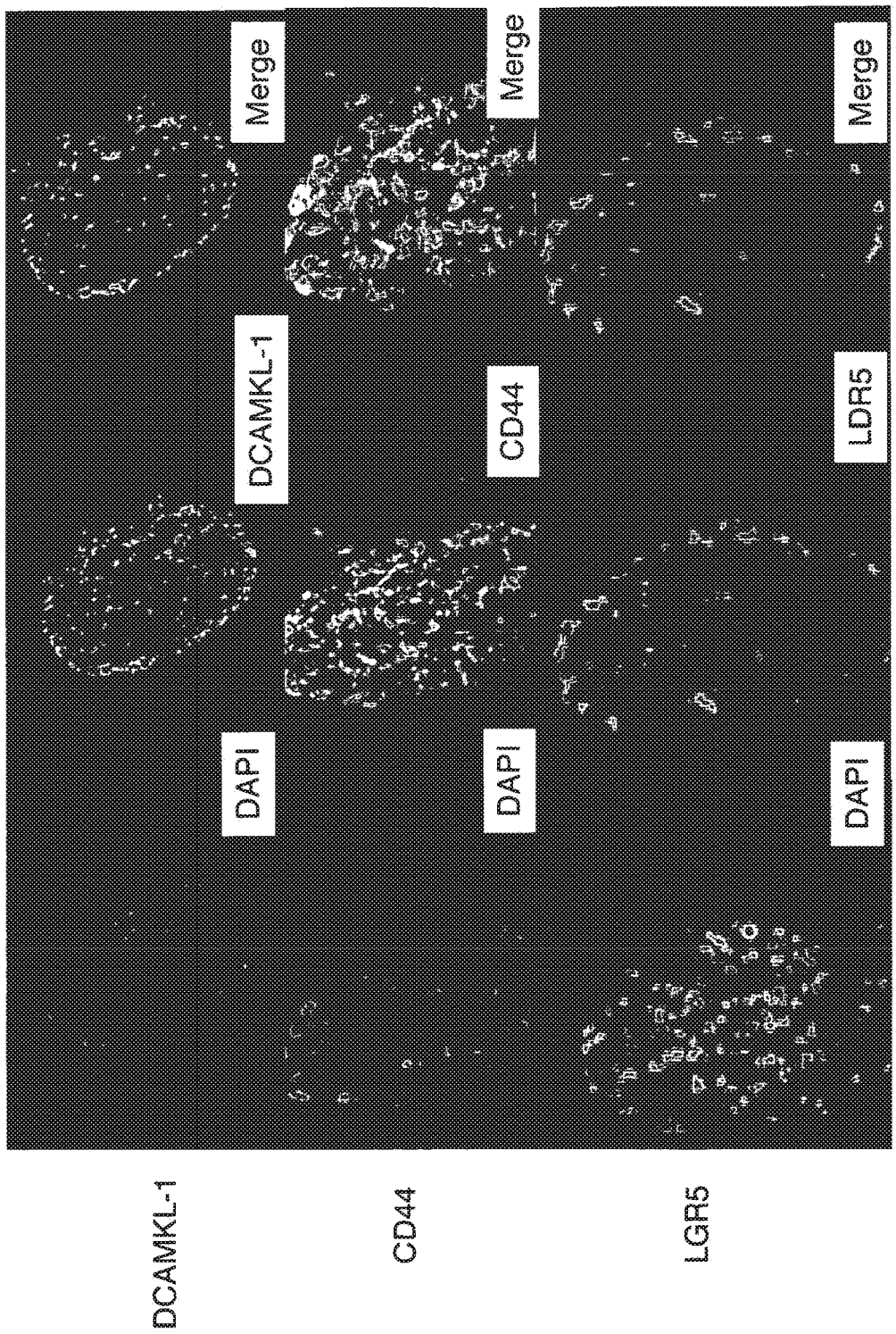

In order to confirm that the stem cell markers chosen can select for stem cell populations that can grow as tumorospheres in non-adherent cultures, populations of stem cells from HCT-116 cells were enriched using FACSorting for DCAMKL1, CD44 and Lgr5, and these cells were grown as tumorospheres. Cells enriched for the specific populations were able to give rise to tumorospheres in vitro (FIG. 12), suggesting that all three cell populations may represent the stem/progenitor cell populations. The tumorospheres from non-sorted colon cancer cells were processed for staining for the stem cell markers, and it was found that while DCAMKL1 and Lgr5 are primarily located at the outer edges of the tumorospheres, CD44 marked almost all the cells in this sphere, suggesting that the DCAMKL1 and Lgr5 may mark for the pluripotent cancer stem cell populations (quiescent or dividing) while CD44 may mark for the rapidly proliferating stem/progenitor cell populations (FIG. 13).

Example 5

Transformed/Cancer Cells Expressing CS-ANXA2 are Also Positive for Stem Cell Markers DCAMKL1, Lgr5 and CD44

Figure 14A:
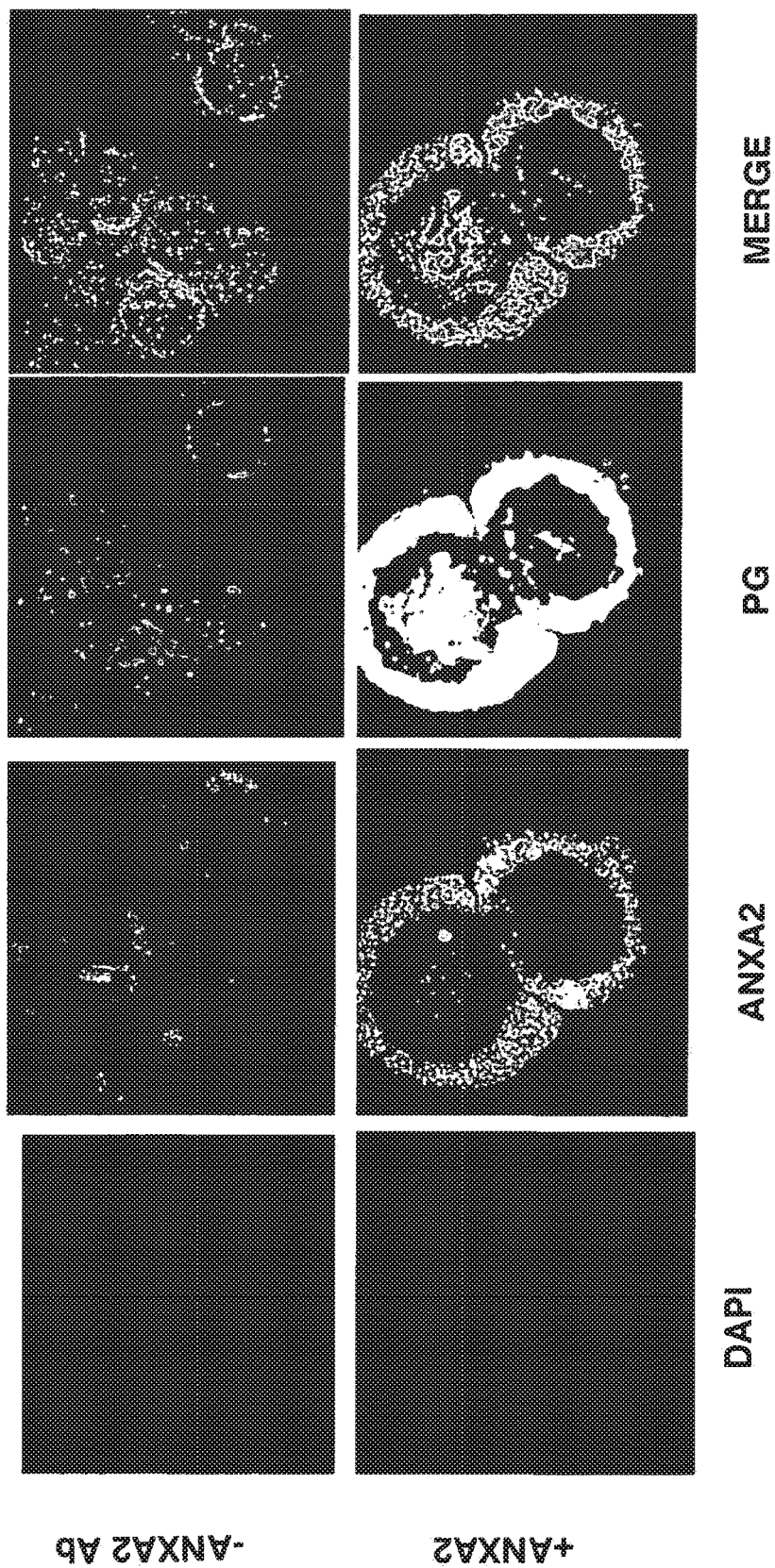
Figure 14B:
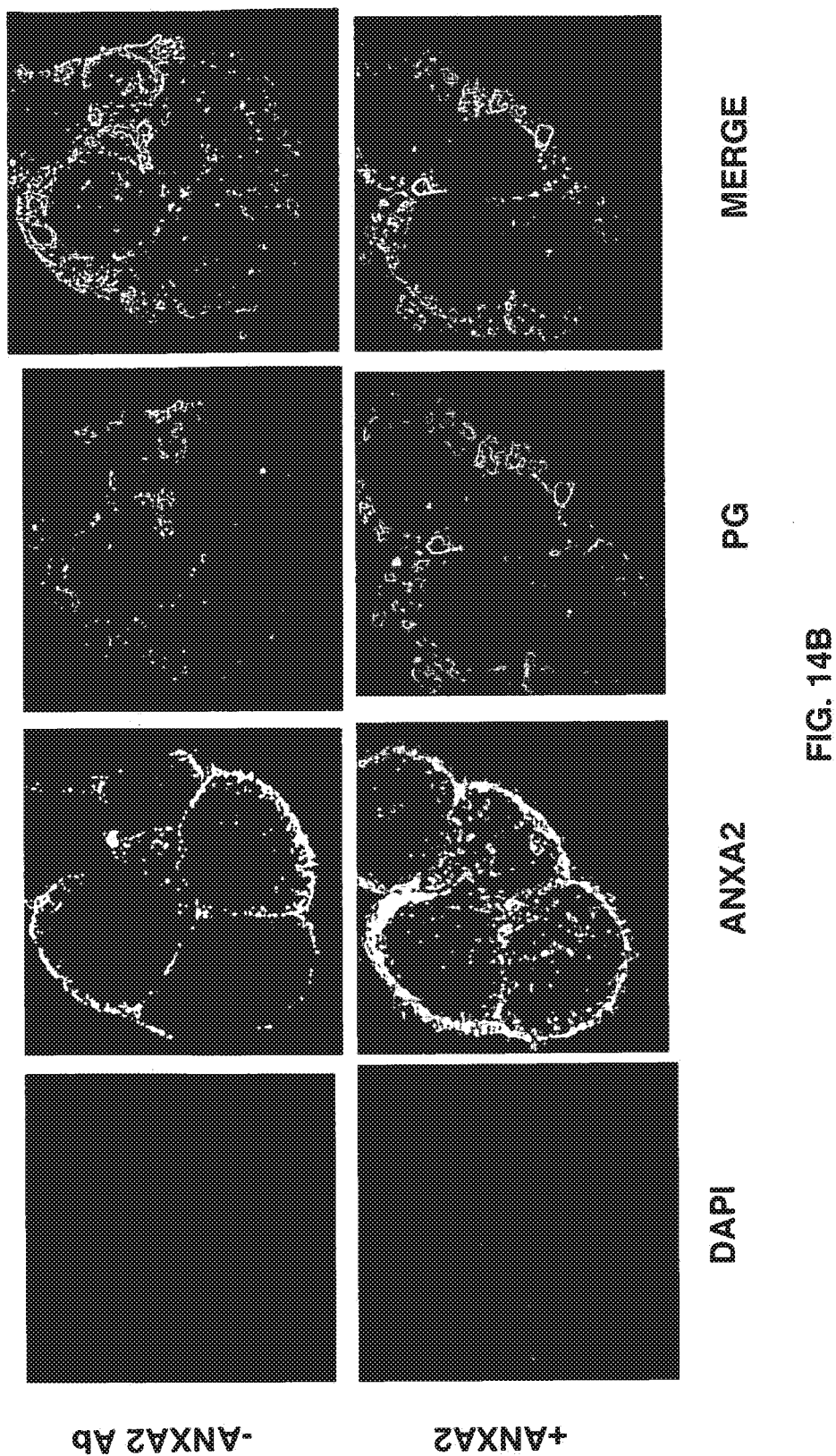
Figure 14C:
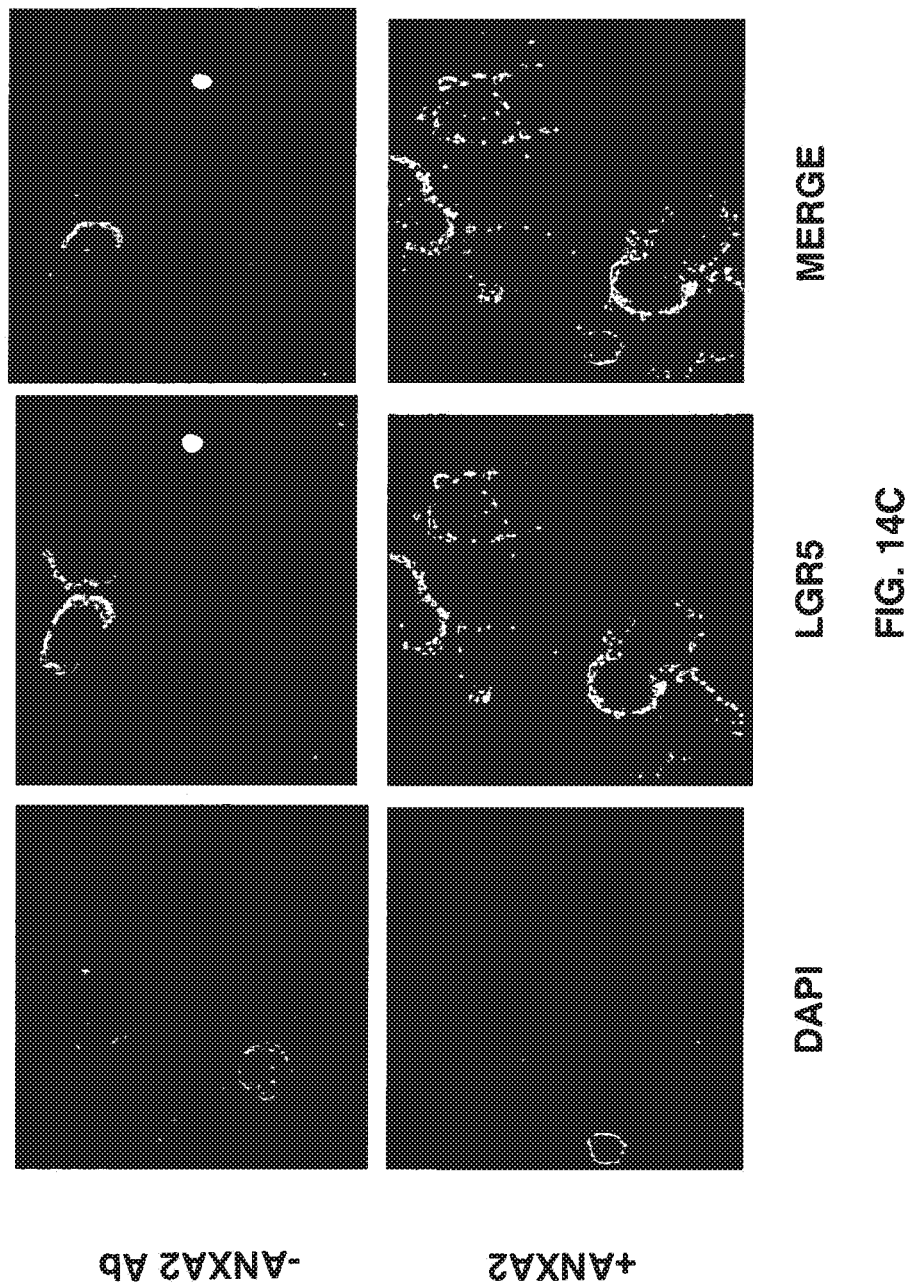

As described above, cancer cell populations enriched in the expression of extracellular domains for DCAMKL1, Lgr5 and CD44 represent cancer stem cell populations which can either actively divide and proliferate or perhaps remain more quiescent (FIGS. 10A-10E, 11-13). At the same time it was demonstrated that tumorigenic/metastatic cells over-expressing CS-ANXA2 may mark for cancer stem cells with a high metastatic potential (FIGS. 8A-8D, 9A-9B). Whether cells enriched for ANXA2 are also positive for the stem cell markers was examined. Cancer cells were FAC-Sorted with anti-ANXA2-IgG for enriching cell populations positive or negative for CS-ANXA2. Cells negative or positive for CS-ANXA2 were cytospun on slides and further stained for the stem cell markers, as shown in FIGS. 14A, B. Cells positive for CS-ANXA2 were also positive for either the extracellular domain of DCAMKL1 (FIGS. 14A-14B) or extracellular domain of the variant forms of CD44 (FIG. 14A-14B) or extracellular domain of Lgr5 (FIG. 14C). On the other hand cells that were negative for the expression of CS-ANXA2 expressed very low levels of DCAMKL1 and CD44 (FIGS. 14A-14B) and Lgr5 (FIG. 14C). Data from several cells analyzed as described for FIGS. 14A-14C are presented in a tabulated form in Table 1. The % cells positive for DCAML-1, CD44 and LGR5 in ANXA2+ and ANXA2- cells, FACSorted from a representative colon cancer cell line are presented in a tabulated form.

TABLE 1

Cells expressing CS-ANXA2 are also positive for stem cell markers
Cancer Cells Sorted with Anti-ANXA2 Antibodies
5 Sorted Cells Stained for Stem Cell Markers

| | ANXA2(+) Cells | ANXA2(+) Cells |
|---|---|---|
| CD44 | 40.6 ± 4 | 15.3 ± 2 |
| DCAMKL1 | 53.1 ± 8 | 20.3 ± 3 |
| LGR5 | 38.8 ± 6 | 18.7 ± |

Thus the results presented herein provide proof of principle data that strongly supports the notion that cancer stem cell populations positive for ANXA2/Lgr5/DCAMKL-1 represent the seed cells which can invade and migrate through the lymphatic and blood vasculature for initiating metastatic growths in the body.

Example 6

Circulating Tumor Cells as a Diagnostic Marker for the Presence of Metastatic Cancer Disease Measuring circulating tumor cells (CTCs) in the blood of patients is a relatively new concept for diagnosing cancer (52-55). Presence of CTCs likely predicts metastasis, and can be useful for monitoring recurrence (relapse) of the disease, post-treatment (56-60). CTCs are detected by using many different methods, including immunocytochemistry (IHC) for epithelial markers such as cytokeratine-19 (CK19), and RT-PCR analysis for cancer-cell specific transcripts (61,62). Efficiency of such tests are poor, because of the rare presence of cancer cells within a very large number of blood cells (1-1000 CTCs in $10^9$ blood cells/ml blood). Negative selection by excluding blood cells has been used to enumerate CTCs (63). Positive selection of CTCs using antibodies (Abs) against epithelial cell surface proteins such as cell adhesion protein EpCAM is currently being used (64). CTCs, positive for EpCAM, are captured using microfluoridic CTC-Chip devices (64) and immunomagnetic bead-based methods (18,57). Isolated CTCs are confirmed by CK19 staining or Her2 amplification (53,65). Negative staining for CD45 (a Leukocyte marker) is also used (52). It is postulated that invasive cancer cells, going through epithelial mesenchymal transition (EMT), lose expression of cell surface EpCAM (66). Thus invasive CTCs, with the highest metastatic potential, may be under-evaluated using anti-EpCAM Abs (52,66,67). Besides, efficacy of different EpCAM-Abs for capturing CTCs differs significantly (68). In order to improve accuracy and sensitivity of CTC assays, expression of cancer cell specific antigens such as PSA (for prostate cancers) (57) or Her2-neu (for breast cancers) (65) are used to analyze captured CTCs. A non-specific adhesion assay (58) and a combination of E-selectin+EpCAM were also developed (69). As described above, the present invention shows that the sensitivity/accuracy of the CTC assay can be significantly enhanced by combining negative selection with positive selection using antibodies against newly identified stem cell markers associated with either quiescent or proliferating cancer stem cell populations as further described below.

As described above, surface associated ANXA2 is increasingly expressed by many solid tumors, including colorectal (CRCs) and pancreatic cancers. ANXA2 lacks transmembrane domains and is tethered to the cell surface by binding to a 26KDa transmembrane protein (11, 31). The present invention shows that membrane-associated ANXA2 is increasingly expressed on transformed (tumorigenic) HEK-mGAS cells vs non-transformed (HEK—C) epithelial cells (FIGS. 7A-7F). CRC cells were isolated with anti-ANXA2-IgG using FACSorting (FIGS. 7A-7F). Surface-associated ANXA2 levels are significantly increased in colorectal Ads and AdCAs vs corresponding normal colonic mucosa (FIGS. 2A-2B). Therefore, invasive/metastatic CTCs are positive for membrane-associated ANXA2 (CS-ANXA2), and that positive selection with anti-ANXA2-Abs rather than anti-EpCAM-Abs significantly increases sensitivity of the CTC assay.

The present invention shows that the presence of Circulating Tumor Stem Cells (CTSCs) can be expected to be diagnostic for recurrent/metastatic disease. Several cancer stem cell markers currently used include CD44/CD133 proteins (48,70-72). However, CD44 and/or CD133 negative cancer cells also give rise to tumorospheres/tumors in vitro and in vivo (73,74), suggesting that these markers may not represent cancer stem cells. CD133 expression is independent of malignant phenotype (75), and a poor marker for survival (76). However, CD133 is a better marker than VEGF and EGFR for predicting metastatic disease (77). More recently, Lgr5 and DCAMKL+1 were discovered as colonic crypt stem cell markers (39-43), and likely play an important role in tumorigenesis, as well (31,43-45). Both Lgr5 and DCAMKL+1 have intra-cellular, transmembrane and extracellular domains. The present invention demonstrates successful isolation of stem/progenitor cells, positive for DCAMKL+1 and Lgr5 by FACSorting (FIGS. 7A-7F, 10A-10E) from human colon cancer and HEK-mGAS cell lines. Spheroidal growths, known to be selective for the growth of stem cells (tumorospheres), were examined with either non-sorted (FIGS. 11,13) or DCAMKL/Lgr5/CD44 sorted (FIG. 12) human colon cancer (HCT-116) cell line. DCAMKL-specific-siRNA disintegrated the tumorospheres (49), suggesting a functional role of DCAMKL1 in maintaining tumorigenic potential of colon cancer cells. DCAMKL1 and Lgr5 positive cells were present only on the periphery, while CD44 cells were dispersed throughout the tumorospheres (FIG. 13) suggesting that DCAMKL/Lgr5 may represent true stem cells.

Example 7

Figure 15A:
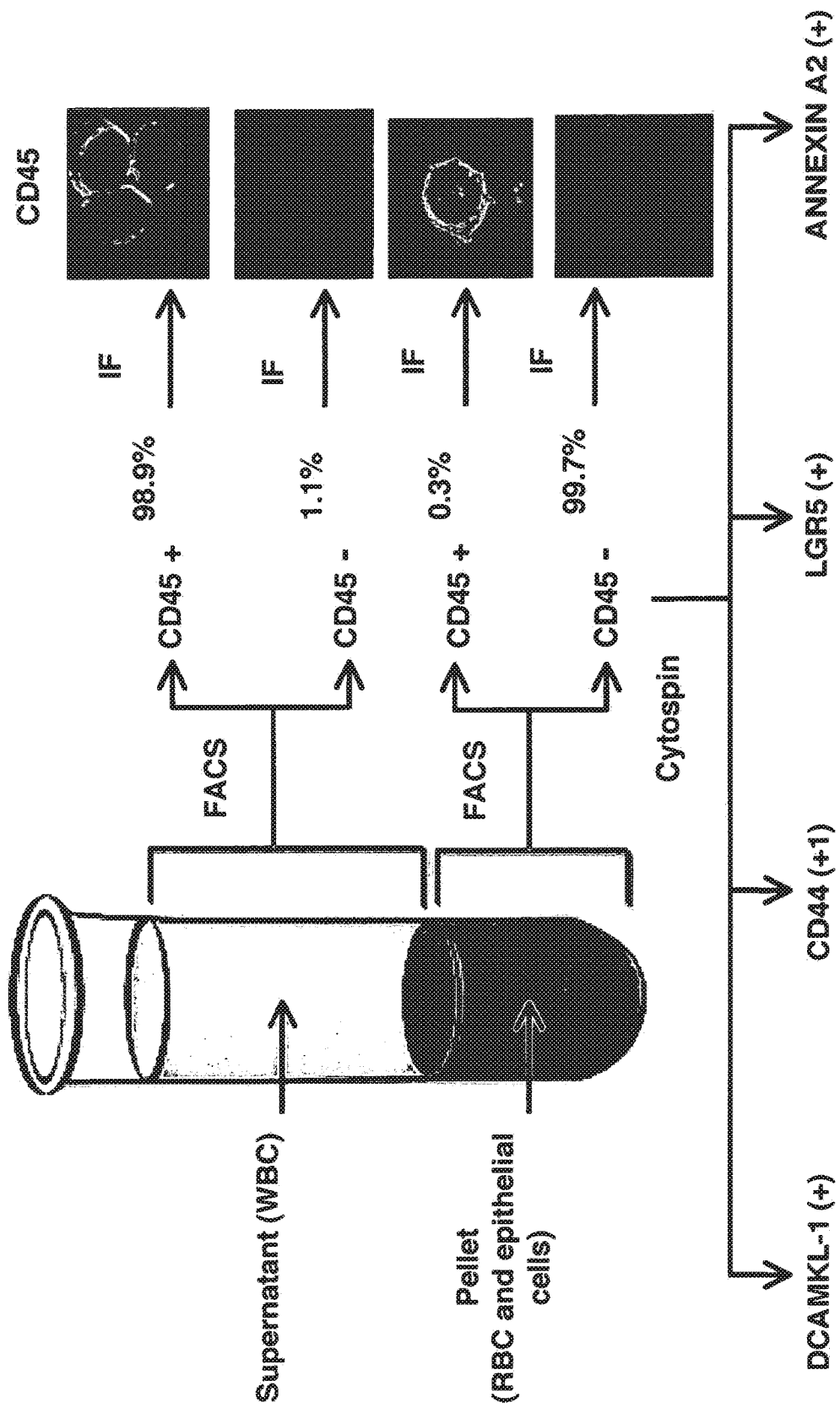
Figures 15B, 15C:
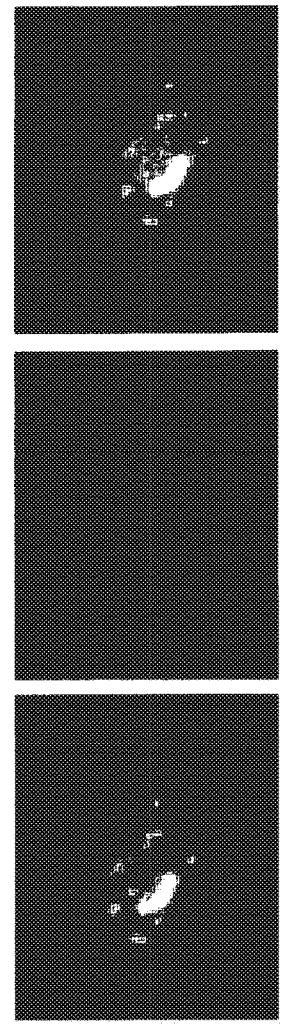
Figure 16:
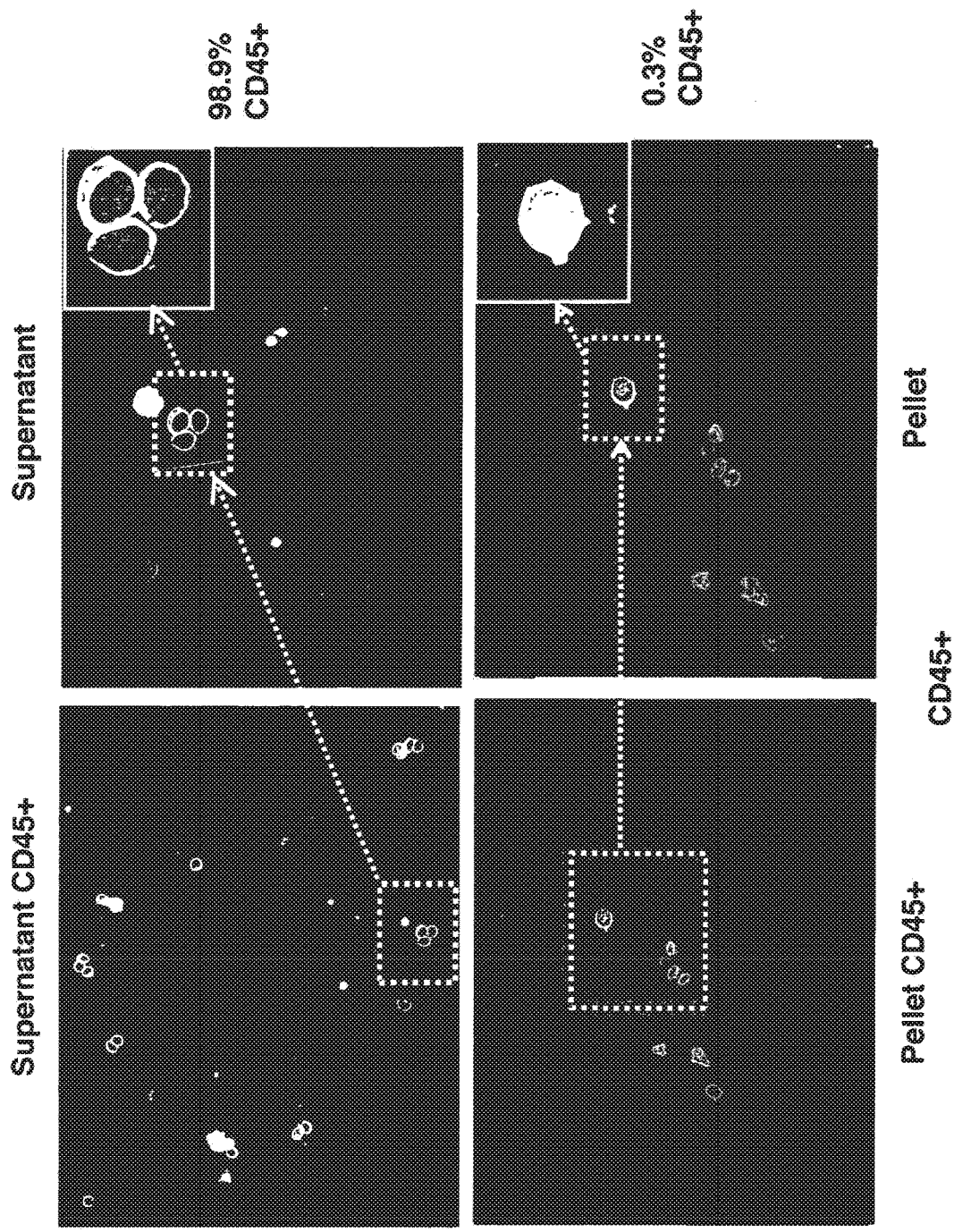

Circulating Tumor Cells (CTCs) Positive for ANXA2, DCAMKL+1, Lgr5 and CD44 are Present in the Blood of Mice Bearing Metastatic Growths The present invention teaches that invasive/metastatic CTCs are positive for membrane associated ANXA2 (CS-ANXA2) and newly identified specific stem cell markers (DCAMKL+1, Lgr5) and the progenitor cancer stem cell marker CD44. Blood was obtained from 3 different groups of mice. Mice in group 1 were sham operated and inoculated with only heat inactivated tumor cells and thus did not grow as tumors. Mice in group 2 were inoculated with $5 \times 10^6$ colon cancer cells on either side of the flank subdermally. Mice in group 3 were inoculated with an equal number of cancer cells in the spleen. Mice in group 3 were inoculated in the spleen and subjected to splenectomy 24 h after inoculation to avoid metastasis into the peritoneum and massive tumorous growths within the spleen itself. In model 3, post-intrasplenic inoculation, it is known that metastatic cancer cells rapidly migrate to the liver and lungs of the mice as shown in FIGS. 8C, 8D and 9A-9B. Mice were euthanized 2 weeks after the inoculation and blood collected from the 3 groups of mice (n=5/group). Blood thus collected was processed as diagrammatically presented in FIGS. 15A-15C. Briefly, ~1 ml blood collected in lithium heparin tube from 2 mice each was centrifuged at ~500 g (1500 rpm) for 5 min at 4° C. and the cells in the supernatant (primarily containing lymphocytes or white blood cells) and cells in the pellet (primarily containing non-nucleated red blood cells and nucleated epithelial cells) were subjected to FACSorting with anti-CD45 antibody, which is known to selectively sort for lymphocytes. The supernatant containing the buffy fraction was >98.9% positive for CD45+ cells, as confirmed by immunofluorescence (IF) staining with CD45 antibody, and only 1.1% of the cells in the supernatant were negative for CD45 staining (FIGS. 15A-15B, 16). On the other hand, cells within the pellet were largely negative for CD45 staining (>99%) and only 0.3% of these cells were still positive for the presence of lymphocytes (FIGS. 15A-15B, 16). The successful separation of white blood cells from the epithelial cells using the simple centrifugation and FACSorting method, which is relatively cheap and easy to perform, is presented more clearly in FIG. 16. This method, while not 100% accurate, is suitable for screening purposes in large populations especially in underdeveloped countries. The pelleted cells that were FACSorted to be negative for CD45 staining were then cytospun on glass slides and immunostained for ANXA2, DCAMKL-1, CD44 and Lgr5 as diagrammatically presented in FIG. 15A. The total number of cells that were positive for the four metastatic/stem cell markers in ~1 ml blood from the 3 groups of mice, labeled N (group 1, normal control mice), PT (group 2, positive for primary tumors growing as sub dermal xenografts), and MT (group 3, positive for metastatic tumors growing in liver or lungs), are presented in FIG. 15B.

Figure 17:
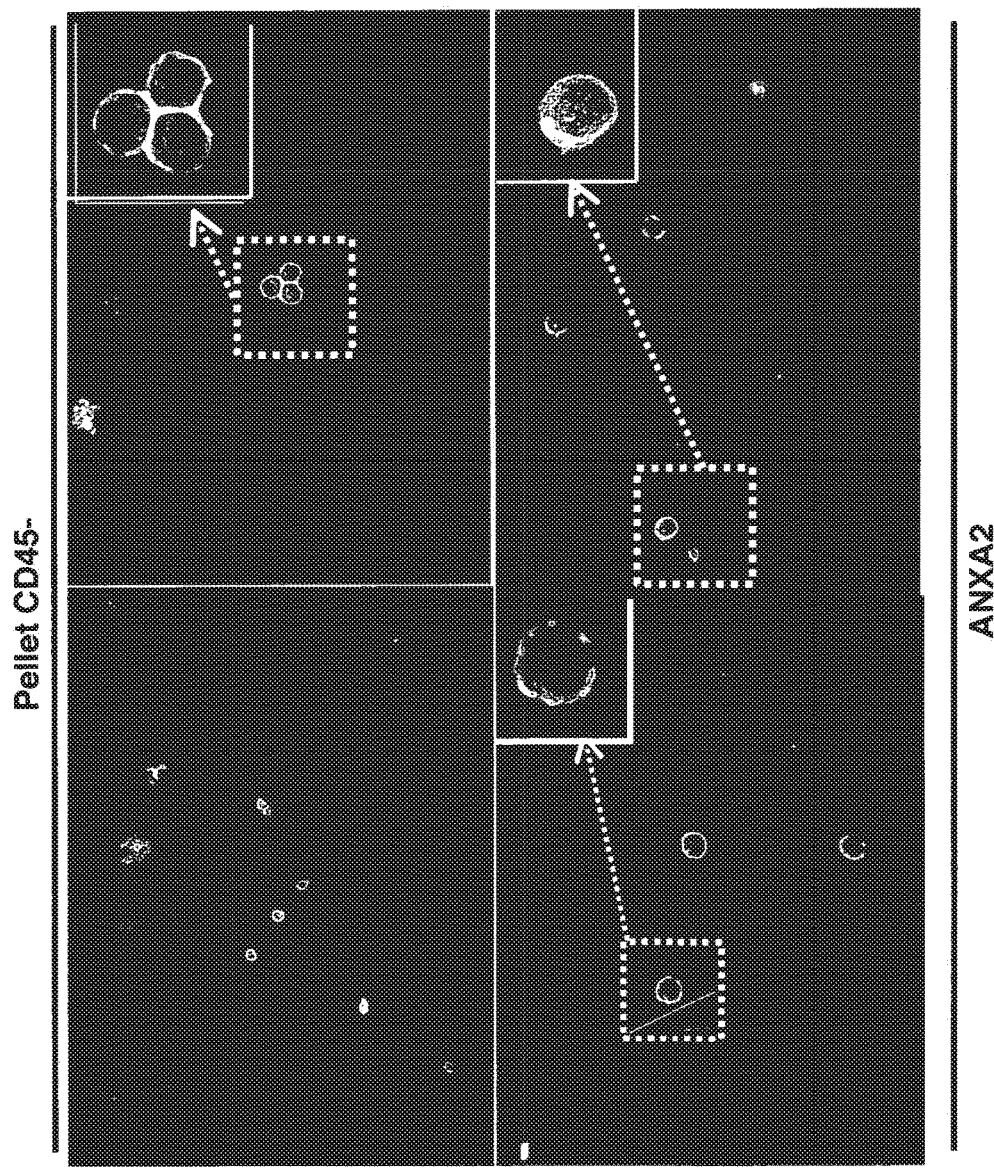
FIG. 17 shows representative images demonstrating the presence of circulating tumor stem cells (CTSCs) in the blood which positively stained for ANXA2 in the CD45− fraction of the pellet, prepared as described in FIG. 15A.
Figure 18:
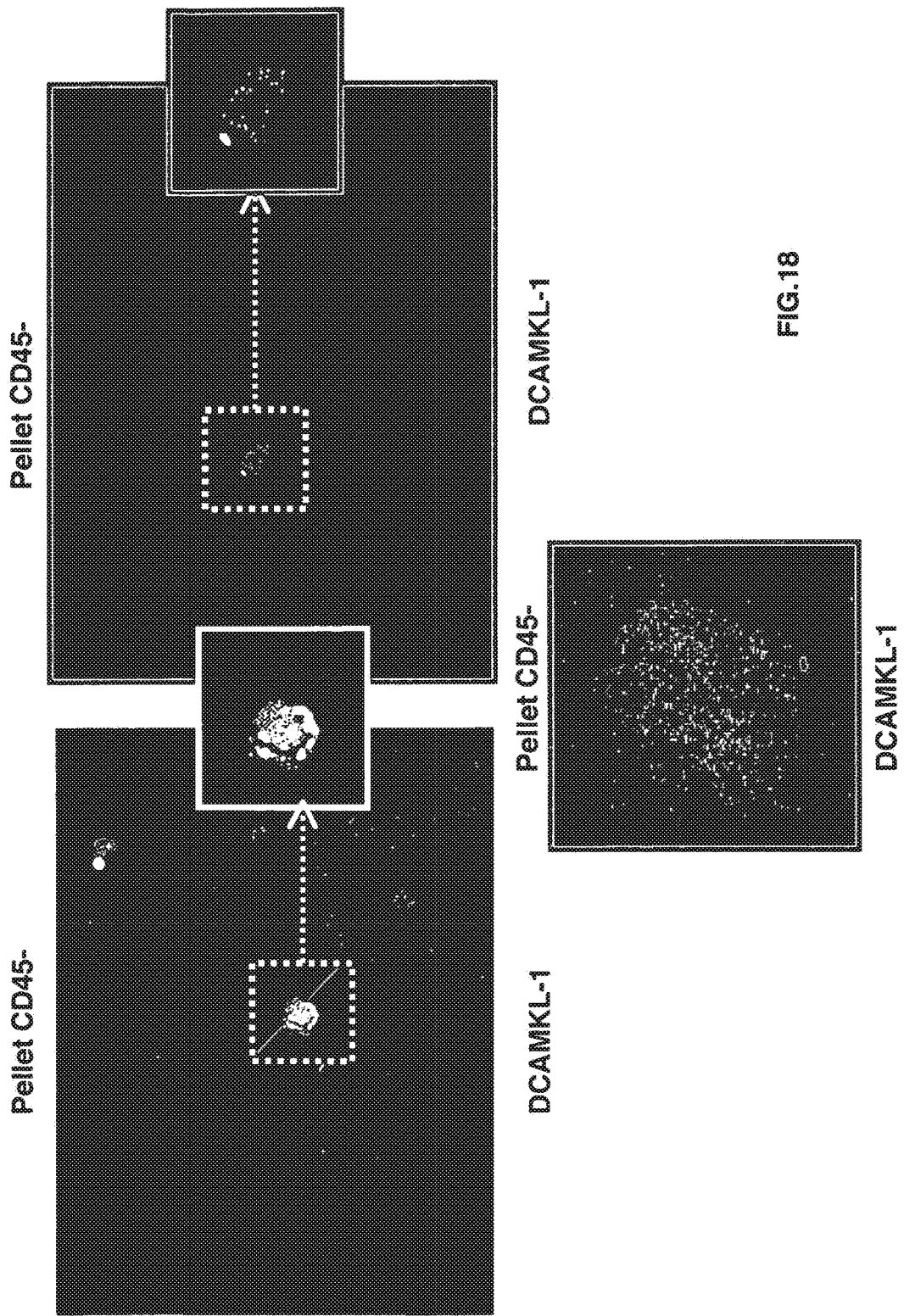
FIG. 18 shows representative images demonstrating the presence of circulating tumor stem cells (CTSCs) in the blood which positively stained for DCAMKL-1 in the CD45− fraction of the pellet, prepared as described in FIG. 15A.
Figure 19:
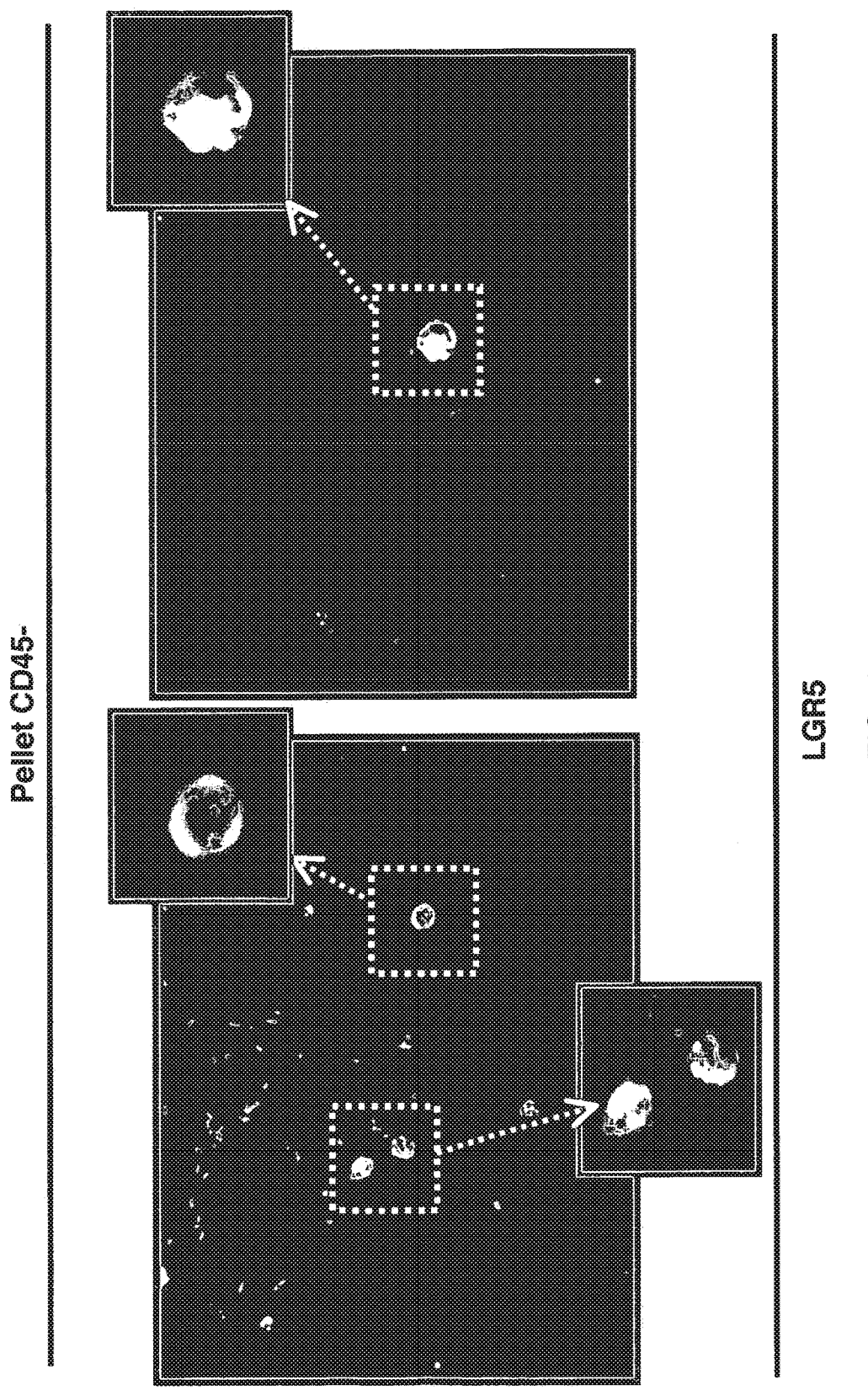
FIG. 19 shows representative images demonstrating the presence of circulating tumor stem cells (CTSCs) in the blood which positively stained for Lgr5 in the CD45− fraction of the pellet, prepared as described in FIG. 15A.
Figure 20:
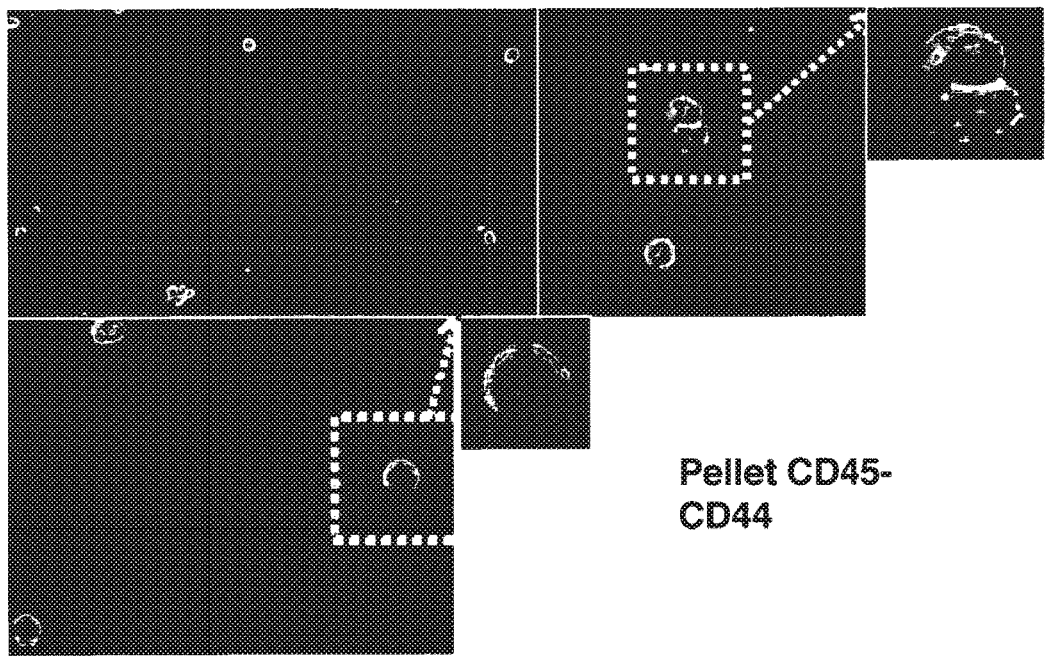
FIG. 20 shows representative images demonstrating the presence of circulating tumor stem cells (CTSCs) in the blood which positively stained for CD44 in the CD45− fraction of the pellet, prepared as described in FIG. 15A.

Representative staining for ANXA2 (FIG. 17), DCAMKL-1 (FIG. 18), Lgr5 (FIG. 19) and CD44 (FIG. 20) are shown for the CD45 negative fraction in the pellets; cells were co-stained with DAP1. As can be seen from data presented in FIGS. 17-20, only the nucleated epithelial cells in this fraction were positive for the indicated stem cell markers (DCAMKL/Lgr5/CD44) and metastatic markers (ANXA2), confirming the accuracy of this method. None of the non-nucleated cells (RBC) were positive for any of these markers. Even though, the pelleted fraction was predominantly (>99%) composed of RBC, one could easily identify the presence of nucleated circulating cancerous epithelial cells which were positive for ANXA2, DCAMKL, CD44 and Lgr5. Importantly, CS-ANXA2 positive circulating tumor cells were also positive for DCAMKL (FIG. 15C).

Based on data presented in FIG. 15B, even the normal blood samples were positive for a minute fraction of cells that were increasingly positive for Lgr5 ($0.2 \times 10^{-6}$), ANXA2 ($0.4 \times 10^{-6}$), and CD44 ($0.6 \times 10^{-6}$), but importantly none were positive for DCAMKL-1. These results suggest that the method used for fractionation, as shown in FIG. 15A, was not 100% effective in removing all the CD45+ cells, as confirmed by staining of the cells in this fraction with anti-CD45-antibody in the pelleted fraction of the blood plasma (FIG. 16). It is known that some lymphocytes also express CD44 and ANXA2 on their cell membranes, which may account for the presence of a minute fraction of CD44 and ANXA2 positive cells in the pellets of blood plasma, perhaps representing a slight contamination with sticky lymphocytes. It is possible that some lymphocytes may also be expressing Lgr5 (perhaps in the hematopoietic stem cell populations), which may account for the very few Lgr5 positive cells in the plasma pellets. But importantly no cells in the plasma pellets from normal blood were positive for DCAMKL-1.

Thus identification of DCAMKL+1 stained cells in the pelleted fraction of plasma will likely represent true cancer stem cell epithelial populations in the blood. Mice in the second group (PT), positive for subdermally located primary xenografts tumors, were increasingly positive for the indicated markers in the order of DCAMKL<Lgr5<ANXA2<CD44, providing further evidence that staining with the stem cell marker DCAMKL may be a more robust identification marker for circulating cancer stem cells, followed by Lgr5 and ANXA2. CD44 appeared to be the least robust marker based on these results, especially for purposes of differentiating between the absence of tumors vs presence of primary/metastatic growths. Importantly, the numbers of DCAMKL+1, Lgr5, CS-ANXA2 and CD44 positive CTCs were highest in mice bearing metastatic tumors (FIG. 15B). Interestingly, the increase in CTCs positive for CS-ANXA2 staining was most significant in mice with metastatic tumors compared to mice with only primary tumors, suggesting that high numbers of CS-ANXA2 positive CTCs may be a selective marker for metastatic disease. The increase in the total number of Lgr5 positive CTCs was also proportionate to the status of the disease in the mice. Importantly, CTCs positive for CS-ANXA2 were also positive for stem cell markers, DCAMKL-1 (FIG. 15C). Thus the data presented in FIGS. 15B-15C, demonstrate that CS-ANXA2 expression in CTCs may mark for cells which are highly metastatic, and thus positive selection of CTCs with CS-ANXA2 along with DCAMKL-1 or Lgr5, will likely provide the most accurate information regarding the numbers of circulating tumor stem cells (CTSCs). Since CTSCs can seed and grow tumors at distant sites more potently than the generic CTCs, this assay is superior to other assays. Based on the results presented in FIGS. 15A-15C, 16-20, the presence of nucleated epithelial cells in the pelleted fraction of the plasma samples obtained from a patient (depleted for lymphocytes with anti-CD45 antibodies) can be best assessed by staining with antibodies against ANXA2+DCAMKL-1 (and/or Lgr5).

Figure 21:
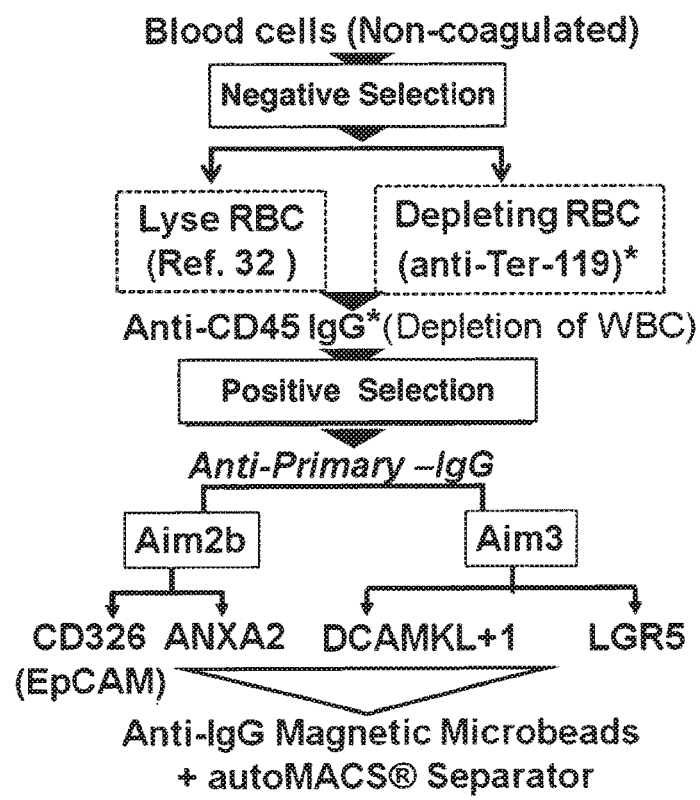
FIG. 21 is a schematic representation of steps taken to isolate Circulating Tumor Stem Cells using antibodies coupled to magnetic micro-beads. *=Abs coupled to magnetic micro-beads from Miltenyi Biotech.

The simple method of analysis presented above for detecting circulating tumor stem cells as a simple laboratory-based non-invasive diagnostic assay for the presence of primary vs metastatic cancerous disease can be further improved by using magnetic micro beads which are coated with specific antibodies against either RBC or white blood cells (CD45) or the stem cell/metastatic markers as diagrammatically presented in the scheme in FIG. 21. The methods presented in FIG. 21 are simpler but require expensive day-to-day tools such as the magnetic micro beads coupled to various antibodies. Many of these beads are available from commercial sources for depleting the blood samples of RBC and white blood cells. Beads coupled to ANXA2 and stem cell marker antibodies are not commercially available but can be easily generated using the specific antibodies available from many sources including our laboratory. It is expected that this method will work just as well or perhaps better than the simplistic method described in FIG. 15A. Results presented in FIGS. 14A-14C, 15A-15C and 16-21 provide strong evidence that the progression of the cancer disease to an advanced stage of cancer due to metastasis and/or recurrence of cancer, post-treatment (relapse), will be reflected by a significant increase in the population of invasive (ANXA2 positive)/circulating cancer stem cells (DCAMKL/Lgr5 positive).

To further validate the use of the markers, blood samples from patients free of any tumorous growths and patients who are positive for benign colonic adenomatous tumors and cancers (adenocarcinomas) were also analyzed. In all cases, patients positive for adenocarcinomas have significantly higher populations of CTCs positive for ANXA2 and stem cell markers DCAMKL-1/Lgr5, compared to that in the blood of healthy patients and patients with only benign adenomatous growths. Blood spiked with NIH3T3 fibroblast cells was used as negative controls.

Thus the presence of DCAMKL-1/Lgr5/ANXA2 positive circulating tumor cells is diagnostic/prognostic for the presence of primary vs metastatic cancer disease and predicts relapse of the disease in patients who had surgical removal or treatment for the cancer previously.

Example 8

Diagnosis of Benign Pre-Cancerous Disease by Measuring AnnexinA2 in the Serum or Plasma While the detection of circulating cancer stem cells, as described above, will be diagnostic/prognostic for the presence of primary vs metastatic cancer disease, it may not be as robust for detecting the presence of benign tumors (at a pre-cancerous stage), such as adenomatous polyps growing in the colon of the patients. The escape of a cancer stem cell or a rapidly dividing tumor cell going through epithelial mesenchymal transition is less likely from a pre-cancerous lesion such as a colonic adenomatous tumor, since the basement membrane in such tumors is still intact. However, the pre-cancerous benign tumorous growths are well vascularized with blood vessels, and tumor-specific antigens can be secreted into the blood supply, albeit at low concentrations. In recent years it has been discovered that significant levels of ANXA2 are present in the serum of patients with breast (2,3), hepatocellular (78) and lung (79) cancers. However, it is not known if individuals positive for benign, pre-cancerous tumorous growths (such as adenomas in the colons, also called colonic polyps, or in situ pancreatic lesions, or benign pre-cancerous growths in the kidneys, lungs and ovaries) are positive for detectable levels of ANXA2 in the blood or serum of the individual. For the first time, the presence of significant levels of ANXA2 in the blood and serum of patients who were positive for pre-cancerous benign tumors in their colons is shown.

Example 9

Cancer Cells/Tumors are the Source of Circulating ANXA2

The present invention shows that cancer cells/tumors are the source of circulating ANXA2 in the blood/serum of individuals. To examine this, conditioned medium (CM) from either colorectal cancer (CRC) or transformed (tumorigenic) epithelial cells (HEK-mGAS) were analyzed. In studies significant concentrations of ANXA2 were measured in conditioned medium (CM) of colorectal cancer and transformed HEK-mGAS cells; non-tumorigenic epithelial cells (HEK—C) were negative (FIG. 22E). Similarly, ANXA2 was measured in secretions of metaplastic bronchial epithelial cells, as an early marker of tumorigenesis (80). Serum was also obtained from patients diagnosed with either hyperplastic (Hp) growths, adenomas (Ads) (pre-cancerous benign tumorous growths) or adenocarcinomas (AdCAs) in the colons. Serum from the latter patients was positive for progressively increasing levels of serum ANXA2 (FIGS. 23A-23B). Similarly, athymic nude mice bearing primary vs metastatic cancers were increasingly positive for serum ANXA2 (FIGS. 23C-23D), while non-tumor bearing mice were negative. The data presented in FIGS. 22A-22E and 23A-23D were either derived by Western Blot analysis or Elisa method of analysis. FIGS. 22A-22D demonstrate standard curves using the Western Blot method while FIG. 24 demonstrates a standard curve using an Elisa assay. To obtain clean-cut results the serum samples were subjected to processing with molecular cutoff membranes using 50Kda and 5Kda membranes to enrich for 36Kda ANXA2 molecule and desalt the samples. The samples were also analyzed using MRM or SRM methods for measuring the tryptic fragments of ANXA2, known to be present in the serum of pateints (based on data presented in Peptide Atlas). However the SRM and MRM methods were much less sensitive and required very high concentrations of ANXA2 in the blood before they could be detected.

Example 10

Diagnosis of Benign Vs Primary Vs Metastic Cancerous Growths, Using Combinatorial Approaches of Analyzing Circulating Cancer Stem Cells and Serum AnnexinA2

The present invention discloses that one may predict the presence of benign (pre-cancerous) growths in a patient by analyzing the levels of serum annexinA2, while predicting the presence of primary vs metastatic cancer disease may be better achieved by analyzing the presence of circulating cancer stem cells using the robust marker, DCAMKL-1, along with annexinA2 which appears to mark for invasive cells; Lgr5 can be used as an additional confirmatory marker. Thus combining the use of all these tests provides a robust assay for separating normal patients (free of benign precancerous growths such as colonic polyps) from patients who may have only the benign disease and patients who may have either primary stage of cancer from a patient who may have a more advanced (metastatic) stage of cancer. At the present time there are no blood based assays which can separate the patients with the various stages of the disease as described above, especially for colo-rectal cancers.

Example 11

Summary

The present invention describes the development of a relatively simple, blood-based, non-invasive method for diagnosing the presence of primary vs metastatic cancers using the presence of circulating tumor stem cells positive for ANXA2/DCAMKL/Lgr5. It is becoming increasingly evident that tumor cells express elevated levels of membrane associated proteins such as Her-2/neu proteins which provide valuable targets for diagnostic/prognostic/treatment purposes in breast cancer. Accumulating evidence suggests that surface associated ANXA2 may serve a similar role for colorectal, pancreatic and lung cancers. An emerging concept is that some of these membrane-associated proteins may also be released into the circulation, providing a non-invasive diagnostic tool for cancers as described for ANXA2 in the present patent application. Measuring the number of circulating tumor cells (CTCs) is another emerging diagnostic tool. Based on the recent identification of tumor surface associated ANXA2 and specific stem cell markers which are elevated in colorectal cancers, one can improve the sensitivity and specificity of a Circulating Tumor Cell (CTC) assay by isolating CTCs from plasma samples with antibodies directed against the newly identified stem cell markers and surface associated ANXA2. This strategy represents an innovative use of recently identified proteins, which will significantly enhance the ability to predict recurrence of metastatic disease, post-treatment.

The present invention thus has many innovative features, which will allow significant improvement in non-invasive methods for diagnosing the presence of primary and metastatic growths from many different cancers including colorectal cancers and pancreatic cancers. Based on these results, CTCs will be positive for extracellular membrane-associated ANXA2 (CS-ANXA2), and that positive selection with anti-ANXA2-Abs will significantly increase the sensitivity of the assays for measuring CTCs in cancer patients. Since recurrence of cancer, post-treatment is likely due to reactivation of dormant/quiescent cancer stem cells, presence of invasive/circulating tumor stem cells (CTSCs), positive for stem cell markers DCAMKL-1/Lgr5 and CS-ANXA2 will be diagnostic/prognostic for re-emergence of the metastatic disease. Currently tumor specific antigens, such as PSA and CEA are used to monitor response of patients to systemic treatments. These methods however are not fool-proof and can provide erroneous data. Analysis of CTCs using the methods described herein can significantly augment the validity of the above assays.

Results obtained from pre-clinical mouse models and patient samples provides strong evidence that negative selection using methods to remove white blood cells and RBCs and positive selection with specific antibodies against ANXA2 and/or specific stem cell markers (DCAMKL-1/Lgr5) will significantly increase the specificity and robustness of an assay for diagnosing and predicting the presence of primary vs metastatic disease and/or relapse. At the present time there are no serum-based diagnostic tests available to predict the presence of benign tumorous growths such as colorectal adenomatous polyps, and the patients have to be subjected to a relatively expensive colonoscopy procedure which requires specific skills and a well-equipped clinic. In the current application strong evidence is provided that the presence of significant levels of ANXA2 in the serum samples of patients is diagnostic for the presence of tumorous growths (benign or cancerous), and could potentially replace the more expensive colonoscopy method in certain settings. In addition, combining the methods of analyzing blood samples for the presence of both circulating tumor stem cells and concentrations of ANXA2 likely provides a robust diagnostic assay for predicting the presence of benign vs cancerous growths in the patient. A screening assay of this type, which is non-invasive and laboratory based, is useful for identifying patients who may need additional tests for confirming the presence of benign and/or cancerous growths.

The following references may have been cited herein:
1. Ortiz-Zapater et al., Am J Pathol. 2007; 170(5):1573-84.
2. Sharma et al., Curr Pharm Des. 2007; 13(35):3568-75.
3. Sharma et al., Exp Mol Pathol. 2006; 81(2):146-56.
4. Inokuchi et al., Int J Cancer. 2009; 124(1):68-74.
5. Frohlich et al., Mol Cell Biol. 1990; 10(6):3216-23.
6. Zhong et al., Arch Oral Biol. 2009; 54(1):17-25.
7. Takano et al., Ann Surg Oncol. 2008; 15(11):3157-68.
8. Zhang et al., J Proteome Res. 2009; 8(11):5041-7.
9. Emoto et al., Cancer. 2001; 92(6):1419-26.
10. Diaz et al., Gut. 2004; 53(7):993-1000.
11. Shiozawa et al., J Cell Biochem. 2008; 105(2):370-80.
12. Singh P. Cancer Lett. 2007; 252(1):19-35.
13. Nedjadi et al., Br J Cancer. 2009; 101(7):1145-54.
14. Zhao et al., Cancer Sci. 2010; 101(2):387-95.
15. Sharma et al., Exp Mol Pathol. 2010; 88(2):278-86.
16. Jacovina et al., J Clin Invest. 2009; 119(11):3384-94.
17. Gerke et al., Physiol Rev. 2002; 82(2):331-71.
18. Singh et al., $101^{st}$ AACR Meeting. April 17-21, 2010. Abstract #2585.
19. Kim et al., Int J Cancer. 2009; 125(10):2316-22.
20. Yan et al., Cancer Res. 2010; 70(4):1616-24.
21. Hajjar et al., J Biol Chem. 1994; 269(33):21191-7.
22. Singh et al., Am. J. Physiol Gastrointest. Liver Physiol 2003: 284, G328-G339.
23. Wu et al., Am J Physiol Gastrointest Liver Physiol. 2003: 285, G1097-G-1110.
24. Singh et al., In: Merchant et al., eds. Gastrin in the New Millennium, (2004), 319-327.
25. Cobb et al., Cancer: 2004; 100:6 1311-1323.
26. Rengifo-Cam et al., Current Pharmaceutical Design 2004: 10, 2345-23358.
27. Rengifo-Cam et al., Cancer Res. 2007, 67:(15), 7266-74.
28. Caplin et al., Br J Surgery. 2000: 87: 1035-40.
29. Koh et al., Can. Res. 2004.6:196-201.
30. Singh et al., Oncogene 2007: 26 (3), 425-440.
31. Sarkar et al., Gastroenterology 2011: 140 (2): 583-595.
32. Singh et al., May 2010 Gastroenterology Vol. 138, Issue 5, Supp. 1, p S-499.
33. Kantara et al., Gastroenterology Vol. 140, 5, Suppl. 1, May 2011. pS-341
34. Sarkar et al., Gastroenterology May 2009, 138, 5, Supplement 1, S-1987.
35. Umar et al., Oncogene 2008: 27, 5599-5611.
36. Umar et al., J. Biol. Chem. 2009; 84 (33):22274-84.

37. Singh et al., Cancer Res. 1986; 46:1612-6.
38. Singh et al., Cancer Res. 1996; 56(18):4111-5.
39. Barker et al., Gastroenterology. 2010; 138(5):1681-96.
40. May et al., Stem Cells. 2008; 26(3):630-7.
41. May et al., Stem Cells. 2009; 27(10):2571-9.
42. Barker et al., Cell Stem Cell. 2010; 6(1):25-36.
43. Fan et al., Int J Colorectal Dis. 2010; 25(5):583-90.
44. Sureban et al., Gastroenterology. 2009; 137(2):649-59, 659.e1-2.
45. May et al., Am J Physiol Gastrointest Liver Physiol. 2010; 299(2):G303-10.
46. Cammareri et al., Methods in Cell Biology. Vol. 86 Chapter 14 pp 311-324. 2008; Elsvier Press.
47. Huang et al., Trends in Mol. Med. 2008; 14: 503-509.
48. Todaro et al., Gastroenterology, 2010; 138; 2151-2162.
49. Zeki et al., Nature Reviews. 2011; 8; 90-100.
50. Soltnian et al., Tumor Biology. 2011; 32: 425-440.
51. Kantara et al., 2011 AACR 102*th Annual Meeting* April 2-6, in Orlando, Fla.
52. Maheswaran et al., Curr Opin Genet Dev. 2010; 20(1): 96-9.
53. Cristofanilli et al., N Engl J Med. 2004; 351(8):781-91.
54. Serrano Fernádez et al., *Clin Transl Oncol.* 2009; 11(10):659-68.
55. Müller et al., Eur J Cancer. 2010; 46(7):1189-97.
56. Scher et al., Lancet Oncol. 2009; 10(3):233-9.
57. Stott et al., Sci Transl Med. 2010; 2(25):25ra23.
58. Lu et al., Int J Cancer. 2010; 126(3):669-83.
59. Tanaka et al., Clin Cancer Res. 2009; 15(22):6980-6.
60. Papavasiliou et al., Proc (Bayl Univ Med Cent). 2010; 23(1):11-4.
61. Ko et al., Oncology. 2000; 59(1):81-8.
62. Maheswaran et al., N Engl J Med. 2008; 359(4):366-77.
63. Yang et al., Biotechnol Bioeng. 2009; 102(2):521-34.
64. Nagrath et al., Nature. 2007; 450(7173):1235-9.
65. Flores et al., Br J Cancer. 2010; 102(10):1495-502.
66. Kokkinos et al., Cells Tissues Organs. 2007; 185(1-3): 191-203.
67. Kalluri et al., J Clin Invest. 2009; 119(6):1420-8.
68. Antolovic et al., BMC Biotechnol. 2010; 10:35.
69. Myung et al., Langmuir. 2010; 26(11):8589-96.
70. Yeung et al., Proc Natl Acad Sci USA. 2010; 107(8): 3722-7.
71. Ricci-Vitiani et al., Nature. 2007; 445(7123):111-5.
72. Dalerba et al., Proc Natl Acad Sci USA. 2007; 104(24): 10158-63.
73. Shmelkov et al., J Clin Invest. 2008; 118(6):2111-20.
74. Navarro-Alvarez et al., Cell Transplant. 2010; 19:865-77.
75. Horst et al., J Pathol. 2009; 219(4):427-34.
76. Salnikov et al., Int J Cancer. 2010; 126(4):950-8.
77. Yasuda et al., Oncol Rep. 2009; 22(4):709-17
78. Ji et al., Int J Mol Med. 2009; 24(6):765-71.
79. Hanash et al., U.S. Pat. No. 6,645,465B2 2003.
80. Kim et al., Biosens Bioelectron. 2009; 25(2):456-62.

Any patents or publications mentioned in this specification are indicative of the levels of those skilled in the art to which the invention pertains. These patents and publications are herein incorporated by reference as if each publication was specifically and individually so incorporated. One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A method for identifying circulating tumor cells, the method comprising:
    processing a subject's blood sample by centrifugation to result in a first population comprising nucleated epithelial cells and a population comprising white blood cells;
    depleting CD45+ cells from the first population to result in a second population substantially depleted of CD45+ cells;
    concentrating the CD45+ depleted population and immunostaining with an anti-CD45 antibody to confirm the relative absence of CD45+ cells;
    measuring CD44 positive cells in the concentrated CD45+ depleted population by contacting the population with an anti-CD44 antibody, and wherein a cell positive for CD44 in the depleted population is a circulating tumor cell.

2. The method of claim 1 wherein the immunostaining comprises immunostaining of cells present on a slide.

3. The method of claim 1 further comprising detecting the presence of epithelial cells in the concentrated population by immunostaining for an epithelial marker.

4. The method of claim 3 wherein the epithelial marker is CK19.

5. The method of claim 4 wherein CK19 is measured using antibody.

6. The method of claim 1 wherein the tumor cells are colorectal tumor cells.

7. A method of identifying circulating tumor cells, the method comprising removing red blood cells from a subject's blood sample to result in a first population including white blood cells and epithelial cells;
    depleting white blood cells from the first population by positive selection of CD45+ cells to result in a second population substantially depleted of CD45+ cells;
    measuring CD44 positive cells in the CD45+ depleted second population by contacting the population with an anti-CD44 antibody, wherein a cell positive for CD44 in the second population is a circulating tumor cell and wherein the depletion of the white blood cells and the measurement of CD44 positive cells comprise the use of antibody-coupled magnetic beads.

8. The method of claim 7 wherein the removal of red blood cells comprises the use of antibody-coupled magnetic beads.

9. The method of claim 7 wherein the tumor cells are colorectal tumor cells.

* * * * *